United States Patent
Oost et al.

(10) Patent No.: US 10,537,590 B2
(45) Date of Patent: Jan. 21, 2020

(54) CYCLIC DINUCLEOTIDE COMPOUNDS

(71) Applicant: BOEHRINGER INGELHEIM INTERNATIONAL GMBH, Ingelheim am Rhein (DE)

(72) Inventors: Thorsten Oost, Biberach an der Riss (DE); Sebastian Carotta, Vienna (AT); Martin Fleck, Warthausen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 15/716,720

(22) Filed: Sep. 27, 2017

(65) Prior Publication Data

US 2018/0092937 A1 Apr. 5, 2018

(30) Foreign Application Priority Data

Sep. 30, 2016 (EP) .................................... 16191919

(51) Int. Cl.
| | | |
|---|---|---|
| *A01N 43/04* | (2006.01) | |
| *A61K 31/70* | (2006.01) | |
| *A61K 31/7084* | (2006.01) | |
| *A61K 31/7076* | (2006.01) | |
| *A61K 39/39* | (2006.01) | |
| *A61K 39/00* | (2006.01) | |

(52) U.S. Cl.
CPC ...... *A61K 31/7084* (2013.01); *A61K 31/7076* (2013.01); *A61K 39/39* (2013.01); *A61K 2039/55561* (2013.01)

(58) Field of Classification Search
None
See application file for complete search history.

(56) References Cited

FOREIGN PATENT DOCUMENTS

| | | |
|---|---|---|
| CA | 2904536 A1 | 11/2014 |
| JP | 2016520085 A | 7/2016 |
| WO | WO-2005087238 A2 * | 9/2005 ......... A61K 31/7076 |
| WO | 2016096174 A1 | 6/2016 |
| WO | 2016145102 A1 | 9/2016 |
| WO | 2017027646 A1 | 2/2017 |

OTHER PUBLICATIONS

International Search Report PCT/EP2017/074608 dated Nov. 9, 2017.
Bussolari, Jacqueline C. et al. "Synthesis and Biological Evaluation of N4-Substituted Imidazo- and v-Triazolo [4,5-d] pyridazine Nucleosides" (1993) Journal of Medical Chemistry, vol. 36, 4113-4120.
Ujjinamatada, Ravi K et al. "Inhibition of Adenosine Deaminase by Analogues of Adenosine and Inosine, Incorporating a Common Heterocyclic Base, 4(7)-Amino-6(5)H-imidazo[4,5-d]pyridazin-7(4)one" J. Med. Chem. (2008) 51, 694-698.

* cited by examiner

*Primary Examiner* — Patrick T Lewis
(74) *Attorney, Agent, or Firm* — Atabak R. Royaee

(57) ABSTRACT

The present invention relates to compounds of general formula I,

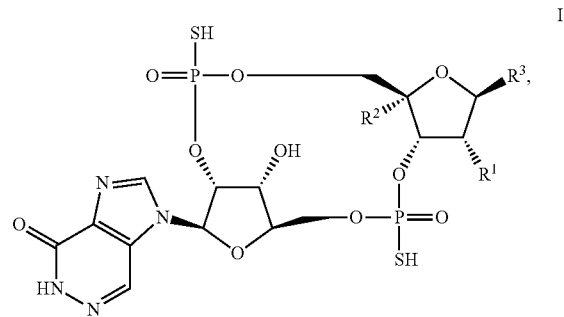

wherein the groups $R^1$, $R^2$ and $R^3$ are defined as in claim 1, which have valuable pharmacological properties, particularly are modulators of STING.

55 Claims, No Drawings

CYCLIC DINUCLEOTIDE COMPOUNDS

FIELD OF THE INVENTION

The present invention relates to novel cyclic dinucleotide compounds ("CDNs") of formula I, including pharmaceutically acceptable salts thereof, that feature the non-purine nucleobase imidazopyridazinone, one purine nucleobase and one non-canonical 2',5' phosphorothioate moiety and induce cytokine production. The present invention further relates to pharmaceutical compositions and combinations containing the compounds of the present invention, and to their medical use for the treatment of diseases associated with or modulated by STING (Stimulator of Interferon Genes). Particularly, the pharmaceutical compositions of the invention are suitable for the therapy of inflammation, allergic and autoimmune diseases, infectious diseases, cancer and as vaccine adjuvants.

BACKGROUND OF THE INVENTION

The role of the immune system is to protect the body from pathogens and malignant cells. However, viruses and cancer cells find ways to evade the immune system. The aim of immunotherapies is thus to initiate an antigen specific immune response or to re-activate a pre-existing response in certain cell types of the immune system against the pathogenic invaders or cancerous cells.

The immune system consists of several specialized lineages which can be roughly grouped into two arms, the innate and the adaptive immune system. For a successful immune reaction lineages from both arms have to act in concert. A major role of the innate immune system is to mount a rapid immune response against pathogens or malignant cells which, unlike the adaptive system, is not antigen specific and long lasting. In addition to the direct killing of pathogens or transformed cells, the innate immune system also activates and subsequently directs the adaptive immune system. Antigen presenting cells such as dendritic cells capture and present antigens in the form of a peptide-major histocompatibility complex (MHC) complex to T cells in lymphoid tissues. This antigen presentation together with the secretion of certain cytokines leads to the activation and differentiation of antigen specific effector CD4 and CD8 T cells. Type I interferon (IFN) production by antigen presenting cells, and other cell types, is considered a key event in the activation of T cells as the lack of type I IFN resulted in a reduced T cell dependent immune response against viral infections or tumor cells (Zitvogel et al, Nature Reviews Immunology 15, 405-414, 2015). On the other hand, the presence of a type I IFN signature during cancer therapy is associated with increased numbers of tumor infiltrating T cells and potentially favorable clinical outcome (Sistigu et al, Nature Medicine 20, 1301-1309, 2014).

Recent studies in mice have shown that efficient secretion of type I IFN in the tumor microenvironment and the induction of a T cell dependent immune response against cancer cells depends on the presence of the adaptor protein stimulator of interferon genes (STING, also known as Tmem173, MPYS, MITA, ERIS)(Woo et al, Immunity 41, 5, 830-842, 2014; Corrales et al, Cell Reports 11, 1018-1030, 2015; Deng et al, Immunity 41, 5, 843-852, 2014). The importance of the presence of type I IFN was highlighted by the fact that the deletion of STING resulted in reduced type I IFN levels in the tumor microenvironment and in a reduced anti-tumor effect in several tumor mouse models. On the other hand, the specific activation of STING resulted in an improved, antigen specific T cell immune response against cancer cells.

STING belongs to the family of nucleic acid sensors and is the adaptor for cytosolic DNA signaling. In its basal state STING exists as a dimer with its N terminal domain anchored in the ER and the C-terminal domain residing in the cytosol. Cyclic dinucleotides (CDNs), generated by the protein cyclic GMP-AMP Synthase (cGAS) are the natural ligands of STING (Ablasser et al, Nature 498, 380-384, 2013). Binding of CDNs to STING induces conformational changes which allows the binding and activation of the TANK binding kinase (TBK1) and interferon regulatory factor 3 (IRF3) and the relocalisation from the ER to perinuclear endosomes (Liu et al, Science 347, Issue 6227, 2630-1-2630-14, 2015). Phosphorylation of the transcription factor IRF3 and NF-kB by TBK1 results in expression of multiple cytokines including type I IFN.

Given the importance of type I IFN in several malignancies including viral infections and cancer therapy, strategies that allow the specific activation of STING is of therapeutic interest.

WO 2014/189805 describes cyclic dinucleotide compounds that feature two purine nucleobases and at least one non-canonical 2',5' phosphodiester or phosphorothioate moiety and induce STING-dependent cytokine production.

WO 2015/185565 describes cyclic dinucleotide compounds that feature two purine nucleobases, one or two cyclopentane instead of ribose tetrahydrofurane rings and one non-canonical 2',5' phosphodiester moiety and modulate STING.

WO 2016/120305 describes cyclic dinucleotide compounds that feature two purine nucleobases, one ribose moiety in which the 2'-OH is replaced with a 2'-F and one non-canonical 2',5' phosphodiester moiety and modulate STING.

US 2014/0329889, WO 2014/099824, WO 2015/017652, Cell 154, 748-762 (2013), and Molecular Cell 51, 226-235 (2013) describe the cyclic dinucleotide 2'3'-cGAMP (cyclic [G(2',5')pA(3',5')p]) which features two purine nucleobases, one canonical 3',5' and one non-canonical 2',5' phosphodiester moieties. Non-canonically linked 2'3'-cGAMP binds to human STING with higher affinity than canonically linked 3'3'-cGAMP or symmetrical bacterial c-di-GMP and induces type I interferon production.

WO 2014/093936 describes cyclic dinucleotide compounds that feature two purine nucleobases and two canonical 3',5' phosphodiester or phosphorothioate moieties and induce STING-dependent cytokine production.

U.S. Pat. No. 7,709,458 describes cyclic dinucleotide compounds that feature two purine nucleobases and two canonical 3',5' phosphodiester moieties and can be used to inhibit cancer cell proliferation or to increase cancer cell apoptosis, in particular the symmetrical bacterial CDN c-di-GMP.

U.S. Pat. No. 7,592,326 describes immunostimulatory cyclic dinucleotide compounds that feature two purine nucleobases and two canonical 3',5' phosphodiester moieties, in particular the symmetrical bacterial CDN c-di-GMP.

WO 2016/096174 and WO 2016/145102 describe cyclic dinucleotide compounds that feature two purine nucleobases and two canonical 3',5' phosphodiester or phosphorothioate moieties and induce STING-dependent cytokine production. Bioorg. Med. Chem. Lett. 18 (2008) 5631-5634 describes immunostimulatory mono- and bisphosphorothioate analogues of symmetrical bacterial CDN c-di-GMP.

SUMMARY OF THE INVENTION

In a first aspect the invention provides cyclic dinucleotide compounds of formula I

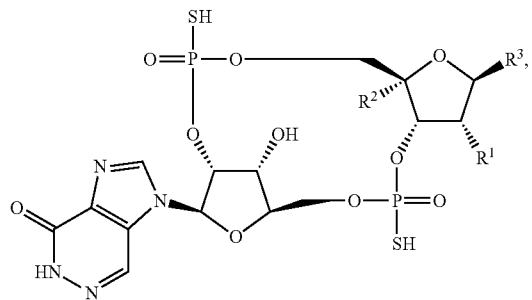

wherein
$R^1$ is selected from the group consisting of H, F, —O—$C_{1-3}$-alkyl and OH, and
$R^2$ is H, or
$R^2$ is —$CH_2$— and $R^1$ is —O—, forming together a —$CH_2$—O— bridge ("Locked Nucleic Acid"; "LNA"), and
$R^3$ is a purine nucleobase selected from the group consisting of purine, adenine, guanine, xanthine, hypoxanthine, connected through its $N^9$ nitrogen;
the isoforms, tautomers, stereoisomers, metabolites, prodrugs, solvates, hydrates, and the salts thereof, particularly the physiologically acceptable salts thereof with inorganic or organic bases, or the combinations thereof.

In a further aspect the invention provides new compounds of formula I, including pharmaceutically acceptable salts thereof, which induce cytokine production in STING-dependent fashion in vitro and/or in vivo and possess suitable pharmacological and pharmacokinetic properties for use in therapy, i.e. for use as medicaments.

In a further aspect the invention provides new compounds of formula I, including pharmaceutically acceptable salts thereof, for use in the treatment of a disease or condition associated with or modulated by STING.

In a further aspect the invention provides new compounds of formula I, or pharmaceutically acceptable salts thereof, for the treatment of inflammation, allergic or autoimmune diseases, for example allergic rhinitis or asthma, for the treatment of infectious diseases or of cancer, or for the use as vaccine adjuvants.

In a further aspect the invention provides a method of treatment of a disease or condition associated with or modulated by STING, in a subject comprising administering a therapeutically effective amount of a compound of formula I, or a pharmaceutically acceptable salt thereof, to the subject.

In a further aspect the invention provides a method of treatment of inflammation, allergic or autoimmune diseases, for example allergic rhinitis or asthma, for the treatment of infectious diseases or of cancer, in a patient in need thereof, comprising administering a therapeutically effective amount of a compound of formula I, or a pharmaceutically acceptable salt, thereof to the patient.

In a further aspect the invention provides pharmaceutical compositions comprising a compound of formula I, or a pharmaceutically acceptable salt thereof, and one or more of pharmaceutically acceptable excipients.

In a further aspect the invention provides the use of a compound of formula I, including pharmaceutically acceptable salts thereof, in the manufacture of a medicament for use in the treatment of a disease or condition in which modulation of STING is beneficial or for use in the treatment of a disease or condition associated with or modulated by STING.

In a further aspect the invention provides the use of a compound of formula I, or pharmaceutically acceptable salts thereof, in the manufacture of a medicament for use in the treatment of inflammation, allergic or autoimmune diseases, for example allergic rhinitis or asthma, for the treatment of infectious diseases or of cancer, or for the use as vaccine adjuvants.

In a further aspect the invention provides a combination comprising a compound of formula I, or a pharmaceutically acceptable salt thereof, and at least one further therapeutic agent.

A further object of the present invention is to provide a pharmaceutical composition comprising a compound of formula I, or a pharmaceutically acceptable salt thereof, and at least one further therapeutic agent and one or more of pharmaceutically acceptable excipients.

In a further aspect the invention provides a combination comprising a compound of formula I, or a pharmaceutically acceptable salt thereof, and at least one further therapeutic agent for use in therapy.

In a further aspect the invention provides a combination comprising a compound of formula I, or a pharmaceutically acceptable salt thereof, and at least one further therapeutic agent for use in the treatment of a disease or condition in which modulation of STING is beneficial or for use in the treatment of a disease or condition associated with or modulated by STING.

In a further aspect the invention provides a combination comprising a compound of formula I, or a pharmaceutically acceptable salt thereof, and at least one further therapeutic agent for use in the treatment of inflammation, allergic and autoimmune diseases, infectious diseases and cancer.

In a further aspect the invention provides a method of treatment of a disease or condition in which modulation of STING is beneficial or of a disease or condition associated with or modulated by STING, in a patient, comprising administering to the patient a therapeutically effective amount of a combination comprising a compound of formula I, or a pharmaceutically acceptable salt thereof, and at least one further therapeutic agent.

In a further aspect the invention provides a method of treatment of inflammation, allergic or autoimmune diseases, infectious diseases or cancer, in a patient, comprising administering to the patient a therapeutically effective amount of a combination comprising a compound of formula I, or a pharmaceutically acceptable salt thereof, and at least one further therapeutic agent.

In a further aspect the invention provides a vaccine adjuvant comprising a compound of formula I, or a pharmaceutically acceptable salt thereof.

In a further aspect the invention provides an immunogenic composition comprising an antigen or antigen composition and a compound of formula I, or a pharmaceutically acceptable salt thereof.

In a further aspect the invention provides an immunogenic composition comprising an antigen or antigen composition and a compound of formula I, or a pharmaceutically acceptable salt thereof, for use in the treatment or prevention of a disease.

In a further aspect the invention provides the use of a compound of formula I, or a pharmaceutically acceptable salt thereof, for the manufacture of an immunogenic composition comprising an antigen or antigen composition, for the treatment or prevention of a disease.

In a further aspect the invention provides a method of treating or preventing a disease comprising the administration to a human subject suffering from or susceptible to a disease, an immunogenic composition comprising an antigen or antigen composition and a compound of formula I, or a pharmaceutically acceptable salt thereof.

In a further aspect the invention provides a vaccine composition comprising an antigen or antigen composition and a compound of formula I, or a pharmaceutically acceptable salt thereof, for use in the treatment or prevention of a disease.

In a further aspect the invention provides the use of a compound of formula I, or a pharmaceutically acceptable salt thereof, for the manufacture of a vaccine composition comprising an antigen or antigen composition, for the treatment or prevention of a disease.

In a further aspect the invention provides a method of treating or preventing a disease comprising the administration to a human subject suffering from or susceptible to disease, a vaccine composition comprising an antigen or antigen composition and a compound of formula I, or a pharmaceutically acceptable salt thereof.

Further objects of the present invention become apparent to the one skilled in the art by the description hereinbefore and in the following and by the examples.

The compounds of the present invention exhibit several advantages, such as favorable binding affinity to human STING, favorable cellular activity, i.e. in cells bearing different human STING alleles, favorable stability in cellular assays, and favorable pharmacokinetic (PK) properties.

DETAILED DESCRIPTION

Unless otherwise stated, $R^1$, and $R^2$ and $R^3$ are defined as above and hereinafter. Some preferred meanings of individual substituents of the compounds according to the invention will be given hereinafter. Any and each of these definitions may be combined with each other.

$R^1$ and $R^2$:

In a first embodiment $R^1$ and $R^2$ are defined as mentioned hereinbefore.

In another embodiment $R^1$ and $R^2$ both are H.

In yet another embodiment $R^1$ is F and $R^2$ is H.

In yet another embodiment $R^1$ is —OH and $R^2$ is H.

In yet another embodiment $R^1$ is —OCH$_3$ and $R^2$ is H.

In yet another embodiment $R^1$ is —O— and $R^2$ is —CH$_2$—, forming together a —O—CH$_2$-bridge.

$R^3$:

In a first embodiment $R^3$ is defined as mentioned hereinbefore.

In another embodiment $R^3$ is purine, connected through its $N^9$ nitrogen.

In another embodiment $R^3$ is adenine, connected through its $N^9$ nitrogen.

In yet another embodiment $R^3$ is guanine, connected through its $N^9$ nitrogen.

In yet another embodiment $R^3$ is xanthine, connected through its $N^9$ nitrogen.

In yet another embodiment $R^3$ is hypoxanthine, connected through its $N^9$ nitrogen.

The following table represents further specified embodiments I-1 to I-16 of the compounds of formula I:

| Embodiment | R | R | R is a purine nucleobase connected through its $N^9$ nitrogen, selected from the group consisting of |
|---|---|---|---|
| I-1 | H | H | purine, adenine, guanine, xanthine, hypoxanthine |
| I-2 | F | H | adenine |
| I-3 | F | H | purine |
| I-4 | F | H | guanine |
| I-5 | F | H | xanthine |
| I-6 | F | H | hypoxanthine |
| I-7 | OH | H | adenine |
| I-8 | OH | H | purine |
| I-9 | OH | H | guanine |
| I-10 | OH | H | xanthine |
| I-11 | OH | H | hypoxanthine |
| I-12 | $R^1$ is —O— and —CH$_2$—, forming together a —O—CH$_2$— bridge | $R^2$ is | adenine |
| I-13 | $R^1$ is —O— and —CH$_2$—, forming together a —O—CH$_2$— bridge | $R^2$ is | purine |
| I-14 | $R^1$ is —O— and —CH$_2$—, forming together a —O—CH$_2$— bridge | $R^2$ is | guanine |
| I-15 | $R^1$ is —O— and —CH$_2$—, forming together a —O—CH$_2$— bridge | $R^2$ is | xanthine |
| I-16 | $R^1$ is —O— and —CH$_2$—, forming together a —O—CH$_2$— bridge | $R^2$ is | hypoxanthine |

A preferred substructure of compounds according to the invention is shown in formula Ia,

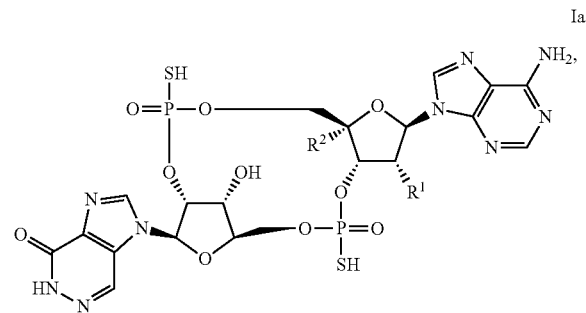

wherein $R^1$ and $R^2$ as well as embodiments thereof are defined as described hereinbefore.

A preferred substructure of compounds according to the invention is shown in formula Ib, Ib

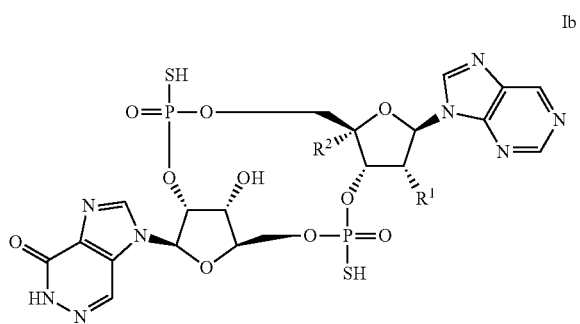

wherein R¹ and R² as well as embodiments thereof are defined as described hereinbefore.

The following compounds according to the invention are particularly preferred:

Ia.1

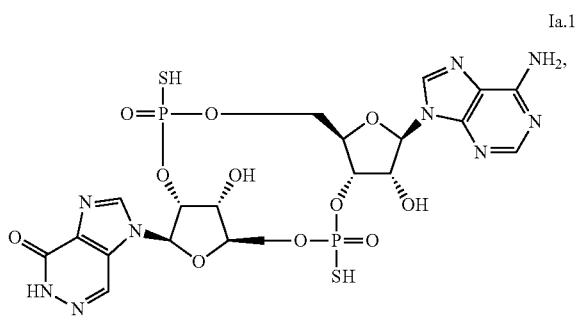

Ia.2

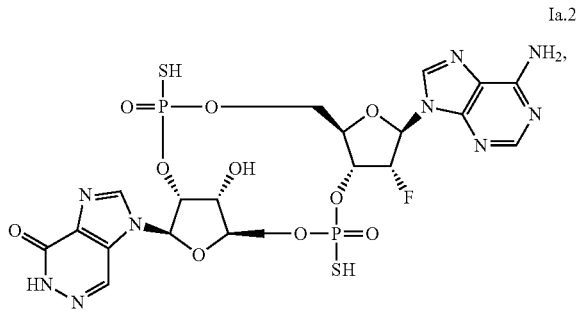

Ia.3 and

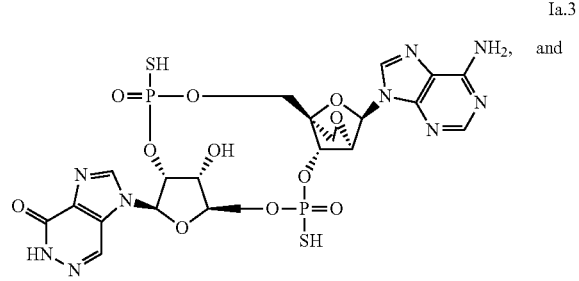

Ib.1

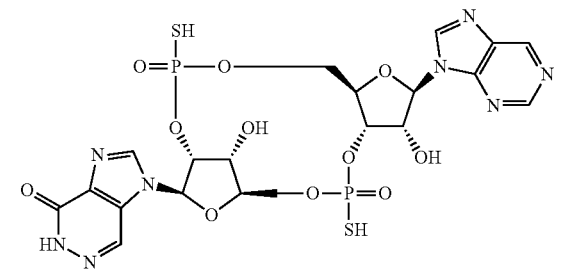

their tautomers and stereoisomers, the salts thereof, particularly the physiologically acceptable salts thereof with inorganic or organic bases, their solvates or hydrates.

The compounds of the present invention possess chiral phosphor atoms with either Rp or Sp configuration. All stereoisomers of the compounds of general formula I, Ia, Ib, Ia.1, Ia.2, Ia.3 and Ib.1, either in substantially pure form or as the mixtures thereof, are covered by the subject invention. The compounds of general formula I, Ia, Ib, Ia.1, Ia.2, Ia.3 and Ib.1 as substantially pure (Rp,Rp), (Rp,Sp), (Sp,Rp) or (Sp,Sp) stereosiomers are preferred, particularly the substantially pure (Rp,Rp) stereoisomer, i.e. both phosphor atoms have the Rp configuration.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled person but are not described in detail here may also be used. The general processes for preparing the compounds according to the invention will become apparent to the skilled person on studying the schemes that follow. Starting compounds are commercially available or may be prepared by methods that are described in the literature or herein, or may be prepared in an analogous or similar manner. Before the reaction is carried out, any corresponding functional groups in the compounds may be protected using conventional protecting groups. These protecting groups may be cleaved again at a suitable stage within the reaction sequence using methods familiar to the one skilled in the art.

Cyclic dinucleotides disclosed herein can be prepared as described in detail below, or by other methods known to those skilled in the art. It will be understood by one of ordinary skill in the art that these schemes are in no way limiting and that variations of detail can be made without departing from the spirit of the present invention.

Cyclic dinucleotide compounds may be obtained by methods described in Chem. Rev. 113, 7354-7401 (2013), Org. Lett., 12, 3269-3271 (2010), Tetrahedron 49, 1115-1132 (1993), WO 2014/189805, WO 2016/096174, WO 2015/185565, WO 2016/145102 or WO 2016/120305 and references cited therein.

The term "protecting group" as used herein, and unless otherwise defined, refers to a chemical functional group that is attached to an oxygen, nitrogen or phosphorus atom to prevent further reaction of that atom, or for other purposes. A wide variety of protecting groups are known to those skilled in the art of organic synthesis, and are described, for example, in "Protective Groups in Organic Synthesis" by T. W. Greene and P. G. M. Wuts, Third Edition, 1999.

The compounds of formula (I) and salts thereof may be prepared by the methodology described hereinafter, constituting further aspects of this invention.

Those who are skilled in the art will recognize that the phosphorothioate moieties in formula (I) may each exist in the R configuration (Rp) or S configuration (Sp). The methodology described hereinafter may yield up to four diastereomers with respect to the phosphor atoms which may be separated by chromatographic methods known to the person who is skilled in the art, for example high pressure liquid chromatography with suitable solvent systems and columns at different stages of the synthesis. In some cases, for example when one sulfurization step proceeds in a diastereoselective fashion, the methodology described hereinafter may preferentially yield only two diastereomers which may be separated by chromatographic methods known to the person who is skilled in the art at different stages of the synthesis.

Substituents not explicitly specified within the following methods of preparation are understood to cover the definitions mentioned hereinbefore under the Summary of the Invention.

A compound of formula

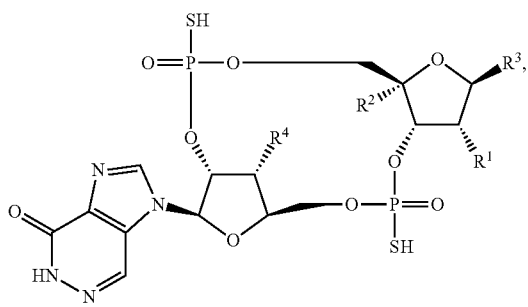

(I')

wherein $R^4$ and optionally $R^1$ are OH, may be prepared by deprotection of a compound of formula (II),

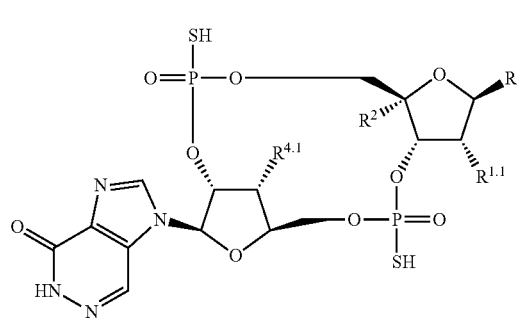

(II)

wherein $R^{4.1}$ and optionally $R^{1.1}$ is oxygen bearing a suitable protecting group, such as tert-butyldimethylsilyl (TBS). For example, $R^{1.1}$ is H, F, O-alkyl or OTBS or, together with $R^2$, forms a —CH$_2$—O— bridge, and $R^{4.1}$ is OTBS. For example, a compound of formula (II) is dissolved in a suitable solvent, for example pyridine, treated with a mixture of triethylamine trihydrofluoride and triethylamine and stirred at a suitable temperature, for example 20-60° C., for a suitable period of time, for example 1-6 hours.

A compound of formula (II) may be prepared by deprotection of a compound of formula (III),

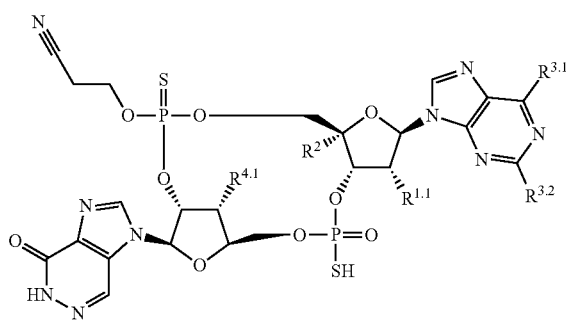

(III)

wherein either $R^{3.1}$ denotes NH bearing a suitable protecting group, such as benzoyl, and $R^{3.2}$ denotes H ("protected adenine") or $R^{3.1}$ denotes OH and $R^{3.2}$ denotes NH bearing a suitable protecting group, such as iso-butyryl ("protected guanine") or $R^{3.1}$ denotes OH and $R^{3.2}$ denotes H ("hypoxanthin") or $R^{3.1}$ and $R^{3.2}$ both denote H ("purine").

For example, a compound of formula (III) is dissolved in a suitable mixture, for example methylamine or aqueous ammonia in methanol or ethanol, and stirred at a suitable temperature, for example 20-60° C., for a suitable period of time, for example 1-24 hours.

A compound of formula (III) may be prepared by cyclization and subsequent sulfurization of a compound of formula (IV), wherein $R^2$, $R^{3.1}$, $R^{3.2}$, $R^{1.1}$ and $R^{4.1}$ are defined as mentioned hereinbefore:

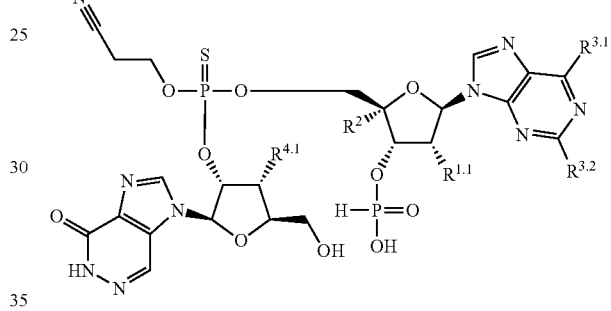

(IV)

For example, a compound of formula (IV) is dissolved in a suitable solvent, for example pyridine, and treated with a suitable coupling reagent, for example 2-chloro-5,5-dimethyl-1,3,2-dioxaphosphorinane 2-oxide (DMOCP) or pivaloyl chloride or adamantoyl chloride, and stirred at a suitable temperature, for example 20° C., for a suitable period of time, for example 0.1-2 hours. The cyclization reaction is quenched by treatment with a suitable sulfurization reagent, for example, 3H-1,2-benzodithiol-3-one or elemental sulfur, and stirred at a suitable temperature, for example 20° C., for a suitable period of time, for example 0.1-2 hours.

A compound of formula (IV) may be prepared by coupling of a compound of formula (V) with a compound of formula (VI), wherein $R^2$, $R^{3.1}$, $R^{3.2}$, $R^{1.1}$ and $R^{4.1}$ are defined as mentioned hereinbefore:

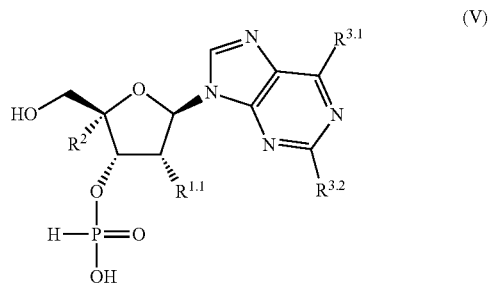

(V)

-continued (VI)

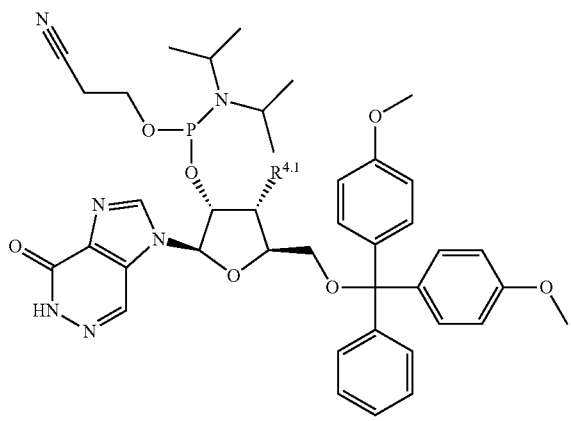

For example, a compound of formula (VI) is dissolved in a suitable solvent, for example acetonitrile, and is treated with a solution of a compound of formula (V) dissolved in a suitable solvent, for example acetonitrile, optionally in the presence of a suitable coupling reagent, for example tetrazole, Activator 42® (activator solution, containing 5-(3,5-bis(trifluoromethyl)phenyl)-1H-tetrazole in acetonitrile), pyridinium dichloroacetate or pyridinium trifluoroacetate (or mixtures of coupling reagents), and stirred at a suitable temperature, for example 20° C., for a suitable period of time, for example 0.1-2 hours. The coupling reaction is quenched by treatment with a suitable sulfurization reagent, for example, 3-((N,N-dimethylaminomethylidene)amino)-3H-1,2,4-dithiazole-3-thione (DDTT) or phenylacetyl disulfide (PADS) or 3H-1,2-benzodithiol-3-one 1,1-dioxide (Beaucage's reagent), and stirred at a suitable temperature, for example 20° C., for a suitable period of time, for example 0.1-2 hours. After evaporation of the solvent, the residue is dissolved in a suitable solvent, for example a mixture of dichloromethane and water, and treated with a suitable reagent, for example dichloroacetic acid, and stirred at a suitable temperature, for example 20° C., for a suitable period of time, for example 0.1-2 hours. A solution containing the product (IV) is obtained by the addition of a suitable solvent, for example pyridine, and concentration by evaporation.

A compound of formula (V) may be prepared by reaction of a compound of formula (VII), wherein $R^2$, $R^{3.1}$, $R^{3.2}$, $R^{1.1}$ and $R^{4.1}$ are defined as mentioned hereinbefore:

(VII)

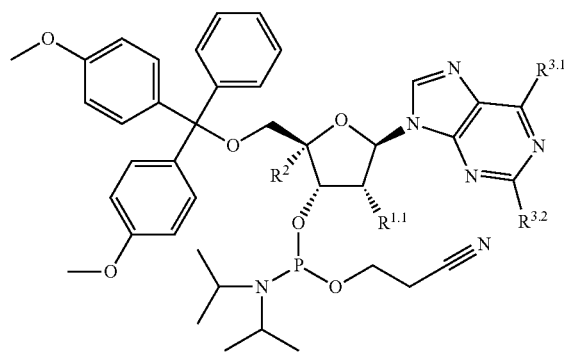

For example, a compound of formula (VII) is dissolved in a suitable mixture, for example acetonitrile containing water, and treated with pyridinium trifluoroacetate, and stirred at a suitable temperature, for example 20° C., for a suitable period of time, for example 1-30 minutes. Then tert-butylamine is added and the mixture stirred at a suitable temperature, for example 20° C., for a suitable period of time, for example 0.1-1 hour. The product is isolated by evaporation of the solvent then dissolved in a suitable solvent, for example dichloromethane containing water, and treated with dichloroacetic acid and stirred at a suitable temperature, for example 20° C., for a suitable period of time, for example 0.1-1 hour. A concentrated solution of the product (V) in acetonitrile is obtained, for example, by the addition of pyridine followed by azeotroping the mixture with acetonitrile.

A compound of formula (VI) may be prepared by reaction of a compound of formula (VIII), wherein $R^{4.1}$ is defined as mentioned hereinbefore:

(VIII)

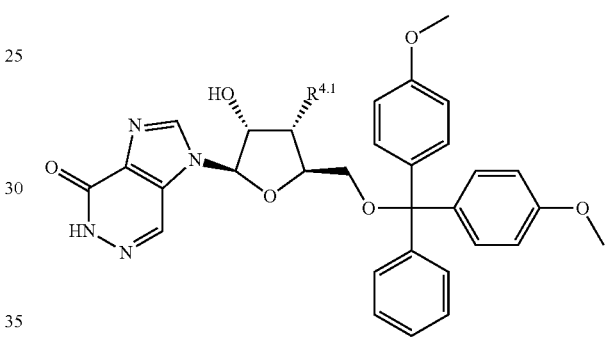

For example, after azeotroping with a suitable solvent, for example acetontrile, a compound of formula (VIII) is dissolved in a suitable solvent, for example dichloromethane, and reacted with a phosphitylating reagent, for example 2-cyanoethyl N,N,N',N'-tetraisopropylphosphorodiamidite, in the presence of an activator, for example 1H-tetrazole, and stirred at a suitable temperature, for example 20° C., for a suitable period of time, for example 1-48 hours.

A compound of formula (VIII) may be prepared by reaction of a compound of formula (IX):

(IX)

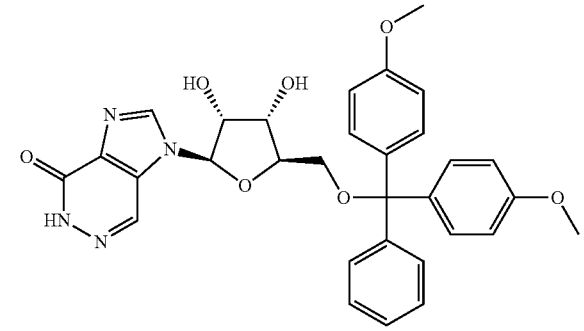

For example, a compound of formula (IX) is dissolved in a suitable solvent, for example, pyridine, and reacted with a suitable silylating reagent, for example tert-butyldimethylsilyl chloride, in the presence of a suitable base, for example imidazole, and stirred at a suitable temperature, for example 20° C., for a suitable period of time, for example 1-48 hours. The regioisomeric 2' and 3'-silylated products are isolated after an aqueous work-up and can be separated, for instance by silica gel chromatography with suitable solvent systems.

A compound of formula (IX) may be prepared by reaction of a compound of formula (X):

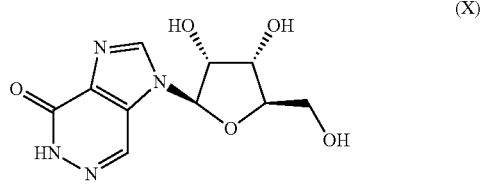 [SMILES: O=c1[nH]ncc2c1ncn2[C@@H]1O[C@H](CO)[C@@H](O)[C@H]1O]

(X)

For example a compound of formula (X) is dissolved in a suitable solvent, for example pyridine, and reacted with 4,4'-dimethoxytrityl chloride, and stirred at a suitable temperature, for example 20° C., for a suitable period of time, for example 1-48 hours.

The compounds of general formula I, or synthetic intermediates thereof, may be resolved into their diastereomers as mentioned below. Diastereomeric mixtures of compounds of general formula I may be resolved into their diastereomers by taking advantage of their different physico-chemical properties using methods known per se, e.g. chromatography and/or fractional crystallization.

As mentioned above, the compounds of formula I may be converted into salts, particularly for pharmaceutical use into the pharmaceutically acceptable salts.

The compounds according to the invention are advantageously also obtainable using the methods described in the examples that follow, which may also be combined for this purpose with methods known to the skilled man from the literature.

Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embrace both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refer to the activation of the STING pathway with one or more compounds of the present invention, in this case representing STING agonists.

The terms "mediated" or "mediating" or "mediate", as used herein, unless otherwise indicated, refer to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

In case a compound of the present invention is depicted in form of a chemical name and as a formula in case of any discrepancy the formula shall prevail.

An asterisk may be used in sub-formulas to indicate the bond which is connected to the core molecule as defined.

Unless specifically indicated, throughout the specification and the appended claims, a given chemical formula or name shall encompass tautomers and all stereo, optical and geometrical isomers (e.g. enantiomers, diastereomers, E/Z isomers etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The term "substantially pure" as used herein with regard to compounds of general formula I refers to one (Rp,Rp), (Rp,Sp), (Sp,Rp) or (Sp,Sp) diastereomer which is at least 75% pure relative to the other possible diastereomers with respect to the phosphor atoms. In preferred embodiments, a substantially pure compounds of general formula I is at least 85% pure, at least 90% pure, at least 95% pure, at least 97% pure, and at least 99% pure.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making salts thereof with bases. The pharmaceutically acceptable salts of the present invention can be synthesized from the parent compound which contains an acidic moiety by conventional chemical methods. Generally, such salts can be prepared by reacting the free acid forms of these compounds with a sufficient amount of the appropriate base in water or in an organic diluent like ether, ethyl acetate, ethanol, isopropanol, or acetonitrile, or a mixture thereof. Alternatively, salts can be prepared by ion exchange, for example by treating aqueous solutions of the compounds of the invention (free acid or salt form) with a cation exchanger.

Pharmacological Activity

Compounds according to the present invention exhibit favorable binding affinity to human STING. The binding affinity can, for instance, be determined by scintillation proximity assay (SPA)-based competition binding assay as described in Nat. Chem. Biol. 10, 1043-1048 (2014). Alternatively, the binding affinity can, for instance, be determined by isothermal titration calorimetry (ITC) as described in Molecular Cell 51, 226-235 (2013). Alternatively, the binding affinity can, for instance, be determined by surface plasmon resonance (SPR) as described in WO 2016/145102. Alternatively, the binding affinity can be determined by differential scanning fluorimetry (DSF), for instance as described in WO 2016/145102.

Compounds according to the present invention exhibit favorable cellular activity. The in vitro cytokine induction can be measured in reporter cell lines, for instance in THP1 cells, in similar fashion as described in WO 2016/096174. Compounds according to the present invention exhibit favorable cellular activity in cells bearing different human STING alleles. Human STING exists in at least five known variants (WT, HAQ, REF/232H, AQ, Q/293 Q). To test the activity of the different CDNs on the human STING variants, THP1-STING KO cells can be stably transduced with vectors encoding for the different STING variants. Furthermore, the in vitro cytokine induction can be measured in human primary PBMCs or human dendritic cells.

Compounds according to the present invention exhibit favorable stability in in vitro cellular assays, for example with THP1 cells, Calu-3 cells or human hepatocytes. Furthermore, compounds according to the present invention exhibit favorable chemical stability in solution and solid state.

Additionally, compounds according to the present invention exhibit favorable pharmacokinetic (PK) properties. The PK properties can be determined in pre-clinical animal species, for example mouse, rat, hamster, dog, guinea pig, mini pig, cynomolgus monkey, rhesus monkey. The PK properties of a compound can be described, for example, by the following parameters: Mean residence time (MRT), elimination half-live ($t_{1/2}$, i.e. the time required for the concentration of the drug to reach half of its original value), volume of distribution ($V_D$, i.e. the apparent volume in which a drug is distributed), area under the curve (AUC, i.e. the integral of the concentration-time curve after a single dose), clearance (CL, i.e. the volume of plasma cleared of the drug per unit time), as described in E. Kerns & L. Di (Drug-like properties: concepts, structure design and methods: from ADME to toxicity optimization, Elsevier, $1^{st}$ ed, 2008).

Certain compounds according to the present invention exhibit favorable in vivo pharmacological activity, for instance in mouse MC38, 4T1, Colon26, EMT6 tumor models after intra-tumoral or intravenous application.

Favorable binding affinity in combination with favorable cellular activity and/or favorable cellular stability and/or improved PK properties can enable lower doses for pharmacological efficacy. Lower doses have the advantages of lower "drug load" or "drug burden" (parent drug and metabolites thereof) for the patient causing potentially less side effects, and lower production costs for the drug product.

The binding of compounds of the invention to human STING may be demonstrated using the following assay:

Differential Scanning Fluorimetry (DSF)

Materials:
Hard-Shell®PCR Plates 384-Well thin-wall (Catalog# HSP3805R, BIO-RAD)
Microseal®'B' Adhesive Seals for PCR Plates (Catalog# MSB-1001, BIO-RAD)
SYPRO orange solution in DMSO (SIGMA cat.-no. S5692-500UL), concentration "5000×"
Instrumentation: Reader: CFX384 Real-Time System (Bio-Rad)
Pipetting Robot: HamiltonStarlet
Assay buffer: 20 mM Tris, 150 mM NaCl pH7.5
Target Protein: Human STING (hSTING, residues 155-341, wild-type sequence with N-terminal His8-tag and TEV-cleavage site, MW: 23601.5 Da)
Protein stock solution: c=309 µM stock solution in assay buffer
Final Assay concentrations of test compounds: 100 uM, 3 uM target protein, "5×" SYPR Orange Assay Procedure:
1) Compound stock solutions and dilutions thereof were prepared in assay buffer
2) 5 ul fluorescent dye stock solution (5000× SYPRO Orange) was mixed with 50 ul target protein (309 uM) and 945 ul buffer.
3) 2 ul of this protein-dye-mixture (25× SYPRO Orange and 15 uM Protein) was added to 8 ul compound solution. Final volume was 10 uL.
4) Certain well positions were used as negative control.
5) The plates were prepared for duplicate measurement and centrifuged for 2 min at 1000 g.
6) In the measurement, 160 cycles of 0.5 degC were used (temperature ramp 15 s/cycle, 15 degC to 95 degC).

Data analysis: The dissociation curves were processed in Bio-Rad CFX Manager.

Peak type was set to "negative". In the case of Example 1.1, Example 2.1 and Example 4.1, at least two Tm measurements were averaged.

The changes in Tm determined are shown in table 1.

TABLE 1

| hSTING Tm shift | |
| --- | --- |
| Example | hSTING Tm shift [° C.] |
| 1.1 | 16.1 |
| 1.2 | 12.0 |
| 2.1 | 23.6 |
| 2.2 | 15.0 |
| 3.1 | 17.0 |
| 3.2 | 9.0 |
| 4.1 | 13.9 |
| 4.2 | 9.0 |
| ML-RR-CDA•2Na$^+$ (Compound 21 in WO 2014/189805) | 12.0 |

The cellular activity of the compounds of the invention may be demonstrated using the following in vitro THP1 assay:

In Vitro Cytokine Induction

The cytokine-induction activities of compounds according to the present invention have been demonstrated by using a THP1 reporter cell line.

Activation of the STING protein expressed in cell lines results in an increase of interferon production. By the stable integration of an interferon regulatory factor (IRF)-inducible SEAP (secreted embryonic alkaline phosphatase) reporter construct the functional interferon signaling pathway can be monitored. Using Invivogen's QUANTI-Blue™ colorimetric enzyme assay and a suitable optical density (OD) reader the activity of SEAP can be detected and quantified. This technique could be used to characterize pharmacological modification of the STING protein.

Measurements of SEAP activity were performed in THP1-Blue ISG cells stably expressing the human STING protein and the IRF-inducible SEAP reporter construct. Cells were cultivated for expansion in RPM11640 medium with 10% fetal calf serum, 50 µg/ml Penicillin-Streptomycin, 100 µg/ml Zeocin, and 100 µg/ml Normocin in a 37°, 95% humidity and 5% $CO_2$ incubator. Assay-ready cells were stored as frozen stocks In preparation for the assay, the cells thawed in Zeocin-/Normocin-free medium and were distributed into the assay plates with a density of 15000 cells/15 µL per well. Compounds were prepared by an 8 or 16 point serial dilution in 50% aqueous DMSO and a final dilution step into medium to ensure a final DMSO concentration of 0.5% in the assay. 5 µL of diluted compounds plus 5 µL medium were added to the plates, followed by a 24 hours incubation at 37° C.

At the day of the assay, 75 µl per well of Quanti-Blue reagent was added to all wells of the plate and the plate was incubated another 30 minutes at 37° C. The OD at 620 nm was measured on the EnVision reader (PerkinElmer).

$EC_{50}$ values and Hill slopes were derived from 8- or 16-point four parametric non-linear curve fittings with the Megalab software (Boehringer Ingelheim) using the OD at 620 nM. The $EC_{50}$ values for Example 1.1, Example 2.1, Example 3.1 and Example 4.1 are the mean of at least two measurements. See Table 2.

TABLE 2

$EC_{50}$ values

| Example | $EC_{50}$ [µM] |
|---|---|
| 1.1 | 0.21 |
| 1.2 | 5.8 |
| 2.1 | 0.05 |
| 2.2 | 0.79 |
| 3.1 | 0.17 |
| 3.2 | 8.5 |
| 4.1 | 0.19 |
| 4.2 | 6.2 |
| ML-RR-CDA•2Na⁺ (Compound 21 in WO 2014/189805) | 0.65 |

In the above THP1 assay, Example 1.1 is more potent than the respective diastereomeric Example 1.2. An X-Ray of Example 1.1 in complex with human STING indicates that both phosphor atoms have the Rp configuration. In analogous fashion it is thus assumed that the more potent respective diastereomers Example 2.1, Example 3.1, Example 4.1 also feature the Rp configuration at both phosphor atoms.

Several single nucleotide polymorphisms have been identified in the human STING gene that may affect the response to cyclic dinucleotides. To determine the activity of compounds of the invention, THP1-BLUE ISG reporter cell lines expressing the different human STING variants have been generated. To do so, the endogenous human STING was first deleted using the CRISPR/CAS9 system: THP1-Blue ISG cells were electroporated with ALL-IN-ONE CRISPR plasmids targeting the STING gene (purchased from Sigma encoding the gRNA and GFP as a reporter gene for successful transduction). GFP positive cells then were sorted 24 h post transfection and expanded. Cells were then dispersed in semisolid methocel medium to allow single cell clone isolations. Clones were then screened for cGAMP responsiveness using the Quanti-blue reporter assay. Non-responsive clones were subsequently analysed for STING loss by western blotting and sequencing of the STING locus.

For the overexpression of the human STING variants, a confirmed THP1-Blue ISG hSTING KO clone was transduced with individual retroviral plasmids (MSCV-ires-GFP-Blasti) encoding the allelic variants of hSTING (WT, HAQ, R232H, AQ and R293Q). Transduced cells were sorted for different levels of GFP fluorescence and STING allele expression was analysed by western blot. Populations expressing ectopic STING protein (WT, HAQ, R232H, AQ and R293Q) at comparable levels to endogenous STING levels form the parental, unmodified THP1-Blue ISG cell lines were selected and used for CDN characterization. Examples of the present invention exhibit cellular activity in all five of the above variants.

Cellular stability of compounds of the invention was measured as follows: The compound was dissolved in cell culture medium (MEM supplemented with 10% FCS, 1% non-essential amino acids and 1% pyruvate) to a final concentration of 10 µM and incubated with human lung epithelial cell line Calu-3 (60000 cells/well in 24-well plate) for up to 24 h. Samples of the cell culture supernatants were taken at 1, 6, 24 h and quantified in LC-MS/MS.

The mouse PK of compounds of the invention was determined using the following method:
Mouse PK
Animal Experiment The compound was dissolved in a solution of physiological NaCl and administered intravenously to male C57BL/6NRj mouse at a dose of 10 µmol/Kg. A 20 µL blood sample was collected at 0.25, 0.5, 0.75, 1 and 2 h by taking ETDA as anticoagulant. Blood plasma was generated by centrifugation and stored at −20° C. The compound concentration was determined by LC-MS/MS. The concentration-time relationships determined (mean of duplicate experiments) are shown in table 3.

TABLE 3

| Example | T = 0.25 h | T = 0.5 h | T = 0.75 h | T = 1 h | T = 2 h |
|---|---|---|---|---|---|
| 1.1 | 3080 nM | 1200 nM | 550 nM | 249 nM | 120 nM |
| 2.1 | 1970 nM | 699 nM | 401 nM | 241 nM | 78 nM |
| 3.1 | 2710 nM | 1280 nM | 595 nM | 260 nM | 111 nM |

Accordingly, the present invention relates to compounds of general formula I as a medicament.

Furthermore, the present invention relates to the use of a compound of general formula I or a pharmaceutical composition according to this invention for the treatment and/or prevention of diseases or conditions which can be influenced by the modulation of STING in a patient or of diseases or conditions associated with or modulated by STING in a patient. Preferably the patient is a human.

In yet another aspect the present invention relates to a method for treating a disease or condition associated with or modulated by STING in a mammal, in need of such treatment, that includes the step of administering to the mammal, preferably a human, a therapeutically effective amount of a compound or a pharmaceutical composition of the present invention.

Diseases and conditions which are associated with or modulated by, or can be influenced by the modulation of STING include inflammation, allergic or autoimmune diseases, for example allergic rhinitis or asthma, infectious diseases or cancer. Furthermore, due to their activity the compounds of the present invention are suitable as vaccine adjuvants.

Autoimmune diseases include, but are not limited to systemic lupus erythmatosus. Psoriasis, insulin-dependent diabetes mellitus (IDDM), dermatomyositis and Sjogren's syndrome (SS).

Inflammation represents a group of vascular, cellular and neurological responses to trauma. Inflammation can be characterised as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterised by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self-tissues. The aim of anti-inflammatory therapy is therefore to reduce this inflammation, to inhibit autoimmunity when present and to allow for the physiological process or healing and tissue repair to progress.

The compounds of the invention may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knew, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic). Ocular inflammation refers to inflammation of any structure of the eye, including the eye lids. Examples of ocular inflammation which may be treated with the compounds of the invention include blepharitis, blepharochalasis, conjunctivitis, dacryoadenitis, keratitis, keratoconjunctivitis sicca (dry eye), scleritis, trichiasis, and uveitis. Examples of inflammation of the nervous system which may be treated with the compounds of the invention include encephalitis, Guillain-Barre syndrome, meningitis, neuromyotonia, narcolepsy, multiple sclerosis, myelitis and schizophrenia.

Examples of inflammation of the vasculature or lymphatic system which may be treated with the compounds of the invention include arthrosclerosis, arthritis, phlebitis, vasculitis, and lymphangitis.

Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionitis, endometritis, epididymitis, omphalitis, oophoritis, orchitis, salpingitis, tubo-ovarian abscess, urethritis, vaginitis, vulvitis, and vulvodynia.

The agents may be used to treat autoimmune conditions having an inflammatory component. Such conditions include acute disseminated alopecia universalise, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, goodpasture's syndrome. Grave's disease, Guillain-Barre syndrome, Hashimoto's disease, Henoch-Schonlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

The agents may be used to treat T-cell mediated hypersensitivity diseases having an inflammatory component. Such conditions include contact hypersensitivity, contact dermatitis (including that due to poison ivy), urticaria, skin allergies, respiratory allergies (hayfever, allergic rhinitis) and gluten-sensitive enteropathy (Celliac disease).

Other inflammatory conditions which may be treated with the agents include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome. Sexary's syndrome, congenital adrenal hyperplasis, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensitivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autroimmine) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis. Type 1 diabetes, asthma, inflammatory bowel disease, systemic lupus erythematosis, psoriasis, chronic pulmonary disease, and inflammation accompanying infectious conditions (e.g., sepsis).

In one aspect the disease or condition to be treated using compounds of the invention is cancer. Examples of cancer diseases and conditions in which compounds of formula I, or pharmaceutically acceptable salts or solvates thereof may have potentially beneficial anti-tumour effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemagioma; hepatoma; fibrosarcoma; chondrosarcoma; myeloma; chronic or acute leukemia; lymphocytic lymphomas; primary CNS lymphoma; neoplasms of the CNS; spinal axis tumours; squamous cell carcinomas; synovial sarcoma; malignant pleural mesotheliomas; brain stem glioma; pituitary adenoma; bronchial adenoma; chondromatous hanlartoma; inesothelioma; Hodgkin's Disease or a combination of one or more of the foregoing cancers.

Preferred cancers, which may be treated with compounds according to the invention, are skin, lung, liver, colon, brain, breast, ovary, prostate cancer, pancreas, kidney, stomach, head, neck and urothelial cancer, as well as lymphoma and leukemia. The new compounds may be used for the prevention, short-term or long-term treatment of the above-mentioned diseases, optionally also in combination with surgery, radiotherapy or other "state-of-the-art" compounds, such as e.g. cytostatic or cytotoxic substances, cell proliferation inhibitors, anti-angiogenic substances, steroids or antibodies.

In their role as adjuvants, in certain embodiments the present compounds and compositions may be used as adjuvants in a therapeutic or prophylactic strategy employing vaccine(s). Thus, the substantially pure CDNs of the present invention, or prodrugs or pharmaceutically acceptable salts thereof, may be used together with one or more vaccines selected to stimulate an immune response to one or more predetermined antigens. The substantially pure CDNs of the present invention, or prodrugs or pharmaceutically acceptable salts thereof, may be provided together with, or in addition to, such vaccines.

Such vaccine(s) can comprise inactivated or attenuated bacteria or viruses comprising the antigens of interest, purified antigens, live viral or bacterial delivery vectors recombinantly engineered to express and/or secrete the antigens, antigen presenting cell (APC) vectors comprising cells that are loaded with the antigens or transfected with a composition comprising a nucleic acid encoding the antigens, liposomal antigen delivery vehicles, or naked nucleic acid vectors encoding the antigens. This list is not meant to be limiting. By way of example, such vaccine(s) may also comprise an inactivated tumor cell that expresses and secretes one or more of GM-CSF, CCL20, CCL3, IL-12p70, FLT-3 ligand, cytokines.

In a related aspect, the present invention relates to methods of inducing, stimulating, or adjuvanting an immune response in an individual. These methods comprise administering the substantially pure CDNs of the present invention, or prodrugs or pharmaceutically acceptable salts thereof, to the individual.

The dose range of the compounds of general formula I applicable per day is usually from 0.0001 to 10 mg, for example from 0.001 to 1 mg. Each dosage unit may conveniently contain from 0.0001 to 10 mg, for example from 0.001 to 1 mg.

The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by mucosal (e.g. oral, sublingual, vaginal, nasal, cervical, etc.), intra-tumoral, peri-tumoral, transdermal, inhalative, or parenteral (e.g. subcutaneous, intravenous, intramuscular, intraarterial, intradermal, intrathecal and epidural administrations) route. In most cases one of the intravenous, intra-tumoral, peri-tumoral or subcutaneous administration routes issuitable.

Pharmaceutical Compositions

For the purposes of this disclosure, the pharmaceutical compositions may be administered by a variety of means including non-parenterally, parenterally, by inhalation spray, topically, or rectally in formulations containing pharmaceutically acceptable carriers, adjuvants and vehicles. Intratumoral (directly into the tumor mass) or peri-tumoral (around the tumor mass) administration of the compounds of the present invention may directly activate locally infiltrating DC, directly promote tumor cell apoptosis or sensitize tumor cells to cytotoxic agents.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and nonaqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

Combination Therapy

The compounds of the invention may be used on their own or may be combined with pharmaceutically acceptable excipients, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the compounds and compositions thereof described herein are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, etc. The compounds and compositions thereof described herein may be administered before, after, and/or simultaneously with an additional therapeutic or prophylactic composition or modality. These include, without limitation, B7 costimulatory molecule, interleukin-2, interferon-g, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleotide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR 9, including lipoprotein, LPS, monophosphoryl lipid A, lipoteichoic acid, imiquimod, resiquimod, and in addition retinoic acid-inducible gene I (RIG-I) agonists such as poly I:C, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619).

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice:A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.). Generally, co-administration or administration together indicates treating a subject with two or more agents, where the agents can be administered simultaneously or at different times. For example, such agents may be delivered to a single subject as separate administrations, which may be at essentially the same time or different times, and which may be by the same route or different routes of administration. Such agents may be delivered to a single subject in the same administration (e.g. same formulation) such that they are administered at the same time by the same route of administration.

Because of the adjuvant properties of the compounds of the present invention, their use may also combined with other therapeutic modalities including other vaccines, adjuvants, antigen, antibodies, and immune modulators. Examples are provided below.

Adjuvants

In addition to the compounds of the present invention and compositions thereof described herein, the compositions or methods of the present invention may further comprise one or more additional substances which, because of their nature, can act to stimulate or otherwise utilize the immune system to respond to the cancer antigens present on the targeted tumor cell(s). Such adjuvants include, but are not limited to, lipids, liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs) and/or pathogen-associated molecular patterns ("PAMPS"). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted bypathogenic and commensal bacterial. Galactosylceramide is an activator of natural killer T (NKT) cells. Muramyl dipeptide is a bioactive peptidoglycan motif common to all bacteria.

Immune Checkpoint Inhibitors

The compounds of the present invention can be used in combination with an immune checkpoint inhibitor, such as an immune checkpoint inhibitor selected from the group consisting of a CTLA-4 pathway antagonist, a PD-1 pathway antagonist, a Tim-3 pathway antagonist, a Vista pathway antagonist, a BTLA pathway antagonist, a LAG-3 pathway antagonist, or a TIGIT pathway antagonist. In some embodiments, the immune checkpoint inhibitor is selected from the group consisting of an anti-CTLA-4 antibody, an anti-PD-1 antibody, an anti-Tim-3 antibody, an anti-Vista antibody, an anti-BTLA antibody, an anti-LAG-3 antibody, or an anti-TIGIT antibody.

The compounds of the present invention can be used in combination with CTLA-4 pathway antagonists. In some embodiments, the combination is used to treat a solid tumor or a hematologic malignancy. CTLA-4 is thought to be an important negative regulator of the adaptive immune response. Activated T cells upregulate CTLA-4, which binds CD80 and CD86 on antigen-presenting cells with higher affinity than CD28, thus inhibiting T-cell stimulation, IL-2 gene expression and T-cell proliferation. Anti-tumor effects of CTLA4 blockade have been observed in murine models of colon carcinoma, metastatic prostate cancer, and metastatic melanoma. In some embodiments, the CTLA-4 pathway antogonist is an anti-CTLA-4 antibody molecule selected from the group consisting of tremelimumab and ipilimumab.

Ipilimumab (a CTLA-4 antibody, also known as MDX-010, CAS No. 477202-00-9) and tremelimumab (IgG2 monoclonal antibody formerly known as ticilimumab, CP-675,206) are humanized monoclonal antibodies that bind to human CTLA4 and prevent its interaction with CD80 and CD86. Other negative immune regulators which may be targeted by a similar strategy include programmed cell death 1 (PD-1), B and T lymphocyte attenuator, transforming growth factor beta, interleukin-10, and vascular endothelial growth factor.

In some embodiments, the compounds of the present invention can be used in combination with an anti-CTLA-4 antibody and an anti-PD-1 antibody. In one embodiment, the combination includes an anti-PD-1 antibody molecule, e.g., as described herein, and an anti-CTLA-4 antibody, e.g., ipilimumab. Exemplary doses that can be use include a dose of anti-PD-1 antibody molecule of about 1 to 10 mg/kg, e.g., 3 mg/kg, and a dose of an anti-CTLA-4 antibody, e.g., ipilimumab, of about 3 mg/kg.

The compounds of the present invention can be used in combination with PD-1 pathway antagonists. In some embodiments, the combination is used to treat a solid tumor or a hematologic malignancy. PD-1 is another negative regulator of adaptive immune response that is expressed on activated T-cells. PD-1 binds to B7-H1 and B7-DC, and the engagement of PD-1 suppresses T-cell activation. Antitumor effects have been demonstrated with PD-1 pathway blockade. Anti-PD-1 antibody molecules (e.g. Nivolumab (Opdivo®), pembrolizumab (Keytruda®), and pidilizumab), and AMP-224 have been reported in the literature to be examples of PD-1 pathway blockers which may find use in the present invention. In some embodiments, the PD-1 pathway antogonist is an anti-PD-1 antibody molecule selected from the group consisting of nivolumab, pembrolizumab or pidilizumab.

In some embodiments the PD-1 pathway antagonist is an immunoadhesin (e.g., an immunoadhesin comprising an extracellular or PD-1 binding portion of PD-LI or PD-L2 fused to a constant region (e.g., an Fc region of an immunoglobulin sequence). In some embodiments, the PD-1 inhibitor is AMP-224 (B7-DCIg; Amplimmune; e.g., disclosed in WO2010/027827 and WO2011/066342) is a PD-L2 Fc fusion soluble receptor that blocks the interaction between PD-1 and B7-H1.

In some embodiments the PD-1 pathway antagonist is a PD-L1 or PD-L2 inhibitor. In some embodiments the PD-L1 or PD-L2 inhibitor is an anti-PD-L1 antibody or an anti-PD-L2 antibody. In some embodiments, the anti-PD-LI inhibitor is chosen from YW243.55.S70, MPDL3280A, MEDI-4736, MSB-0010718C, or MDX-1105. In some embodiments, the PD-L1 inhibitor is an anti-PD-L1 antibody MSB0010718C. MSB0010718C (also referred to as A09-246-2; Merck Serono) is a monoclonal antibody that binds to PD-L1.

The compounds of the present invention can be used in combination with TIM-3 pathway antagonists. In some embodiments, the combination is used to treat a solid tumor or a hematologic malignancy. In some embodiments, the TIM-3 pathway antagonist is an anti-TIM-3 antibody. In some embodiments, anti-TIM-3 antibody molecules are disclosed in US 2015/0218274, published on Aug. 6, 2015, entitled "Antibody Molecules to TIM-3 and Uses Thereof".

The compounds of the present invention can be used in combination with LAG-3 pathway antagonists. In some embodiments, the combination is used to treat a solid tumor or a hematologic malignancy. In some embodiments, the LAG-3 pathway antagonist is an anti-LAG-3 antibody. In some embodiments the anti-LAG-3 antibody molecules are disclosed in US 2015/0259420, filed Mar. 13, 2015, entitled "Antibody Molecules to LAG-3 and Uses Thereof".

Amino Acid Catabolism

The compounds of the present invention can be used in combination with an amino acid metabolism inhibitor such as an IDO or Arginase1 or Arginase2 inhibitor to antagonise the immune inhibitory effect of immune suppressive immune cells such as myeloid derived suppressor cells.

Purinergic Signalling Pathway

The compounds of the present invention can be used in combination with inhibitors of the purinergic signalling pathway such as CD39 and CD73 pathway antagonists or A2A/A2B receptors inhibitors.

Chemokines and Chemokine Receptors

The compounds of the present invention can be used in combination with chemokine or chemokine receptor antagonist to inhibit the recruitment of suppressive immune cells into the tumor microenvironment. For example, but not exclusively, the compounds of the present invention can be used in combination of CCR2 or CCR5 antagonist the reduce the infiltration of myeloid suppressor cells and regulatory T cells.

T-Cell Receptor Agonists

The compounds of the present invention can be used in combination with a T-cell receptor agonist, such as a CD28 agonist, an OX40 agonist, a GITR agonist, a CD137 agonist, a CD27 agonist or an HVEM agonist.

The compounds of the present invention can be used in combination with a CD27 agonist. Exemplary CD27 agonists include an anti-CD27 agonistic antibody, e.g. as described in PCT Publication No. WO 2012/004367.

The compounds of the present invention can be used in combination with a GITR agonist. In some embodiments, the combination is used to treat a solid tumor or a hematologic malignancy. Exemplary GITR agonists include, e.g., GITR fusion proteins and anti-GITR antibodies (e.g., bivalent anti-GITR antibodies).

TLR Agonists

The compounds of the present invention can be used in combination with a Toll like receptor agonist. The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-1R) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

TLR agonists known in the art and finding use in the present invention include, but are not limited to, the following:

Pam3Cys, a TLR-1/2 agonist;
CFA, a TLR-2 agonist;
MALP2, a TLR-2 agonist;
Pam2Cys, a TLR-2 agonist;
FSL-1, a TLR-2 agonist;
Hib-OMPC, a TLR-2 agonist;
polyribosinic:polyribocytidic acid (Poly I:C), a TLR-3 agonist;
polyadenosine-polyuridylic acid (poly AU), a TLR-3 agonist;
Polyinosinic-Polycytidylic acid stabilized with poly-L-lysine and carboxymethylcellulose
(Hiltonol®), a TLR-3 agonist;
monophosphoryl lipid A (MPL), a TLR-4 agonist;
LPS, a TLR-4 agonist;
bacterial flagellin, a TLR-5 agonist;
sialyl-Tn (STn), a carbohydrate associated with the MUC1 mucin on a number of human
cancer cells and a TLR-4 agonist;
imiquimod, a TLR-7 agonist;
resiquimod, a TLR-7/8 agonist;
loxoribine, a TLR-7/8 agonist; and
unmethylated CpG dinucleotide (CpG-ODN), a TLR-9 agonist.

Because of their adjuvant qualities, TLR agonists are preferably used in combinations with other vaccines, adjuvants and/or immune modulators, and may be combined in various combinations. Thus, in certain embodiments, the mono- or di-FCDN compounds that bind to STING and induce STING-dependent TBK1 activation and an inactivated tumor cell which expresses and secretes one or more cytokines which stimulate dendritic cell induction, recruitment and/or maturation, as described herein can be administered together with one or more TLR agonists for therapeutic purposes.

Antibody Therapeutics

The compounds of the present invention can be used in combination with therapeutic antibodies. In some embodiments, the mechanism of action of the therapeutic antibody is Antibody-Dependent Cell-Mediated Cytotoxicity (ADCC). ADCC is a mechanism of cell-mediated immune defense whereby an effector cell of the immune system actively lyses a target cell, whose membrane-surface antigens have been bound by specific antibodies. It is one of the mechanisms through which antibodies, as part of the humoral immune response, can act to limit and contain infection. Classical ADCC is mediated by natural killer (NK) cells; macrophages, neutrophils and eosinophils can also mediate ADCC. ADCC is an important mechanism of action of therapeutic monoclonal antibodies, including trastuzumab and rituximab, against tumors. Compounds of the present invention may act to potentiate ADCC.

The following are an exemplary list of antibodies which may be used together with the compounds of the present invention:

Muromonab-CD3, Infliximab, adalimumab, Omalizumab, Daclizumab, Rituximab, Ibritumomab, Tositumomab, Cetuximab, Trastuzumab, Alemtuzumab, Lym-1 Ipilimumab, Vitaxin, Bevacizumab and Abciximab.

Additional therapeutic antibodies that may be used in combination with the compounds of the present invention include a prolactin receptor (PRLR) inhibitor, a HER3 inhibitor, an EGFR2 and/or EGFR4 inhibitor, an M-CSF inhibitor, an anti-APRIL antibody, or an anti-SIRPα or anti-CD47 antibody.

Chemotherapeutic Agents

In additional embodiments of the methods described herein, the compounds of the present invention are used in combination with chemotherapeutic agents (e.g. small molecule pharmaceutical compounds). Thus the methods further involve administering to the subject an effective amount of one or more chemotherapeutic agents as an additional treatment or a combination treatment. In certain embodiments the one or more chemotherapeutic agents is selected from the group consisting of abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-tbutylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), enzalutamide, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

In additional embodiments the methods described herein, the compounds of the present invention are used in combination with chemotherapeutic agents and/or additional agents for treating the indications as described in the methods herein. In some embodiments, the compounds of the present invention are used in combination with one or more agents selected from the group consisting of sotrastaurin, nilotinib, 5-(2,4-dihydroxy-5-isopropylphenyl)-N-ethyl-4-(4-(morpholinomethyl)phenyl)isoxa-zole-3-carboxamide, dactolisib, 8-(6-Methoxy-pyridin-3-yl)-3-methyl-1-(4-piperazin-1-yl-3-trifluoromethyl-phenyl)-1,3-dihydro-imidazo[4,5-c]quinolin-2-one, 3-(2,6-dichloro-3,5-dimethoxyphenyl)-1-(6-((4-(4-ethylpiperazin-1-yl)phenyl)amino)pyrimidin-4-yl)-1-methylurea, buparlisib, 8-(2,6-difluoro-3,5-dimethoxyphenyl)-N-(4-((dimethylamino)methyl)-1H-imidazol-2-yl)quinoxaline-5-carboxamide, (S)—N1-(4-methyl-5-(2-(1,1,1-trifluoro-2-methylpropan-2-yl)pyridin-4-yl)thiazol-2-yl)pyrrolidine-1,2-dicarboxamide, (S)-1-(4-chlorophenyl)-7-isopropoxy-6-methoxy-2-(4-(methyl-(((1r,4S)-4-(4-methyl-3-oxopiperazin-1-yl)cyclohexyl)methyl)amino)phenyl)-1,2-dihy-droisoquinolin-3(4H)-one, deferasirox, letrozole, (4S,5R)-3-(2'-amino-2-morpholino-4'-(trifluoromethyl)-[4,5'-bipyrimidin]-6-yl)-4-(hydroxymethyl)-5-methyloxazolidin-2-one, (S)-5-(5-chloro-1-methyl-2-oxo-1,2-dihydropyridin-3-yl)-6-(4-chlorophenyl)-2-(2,4-dimethoxypyrimidin-5-yl)-1-isopropyl-5,6-dihydropyrrolo[3,4-d]imidazol-4(1H)-one, 4-((2-(((1R,2R)-2-hydroxycyclohexyl)amino)benzo[d]thiazol-6-yl)oxy)-N-methylpicolin-amide, imatinib mesylate, 2-fluoro-N-methyl-4-(7-(quinolin-6-ylmethyl)imidazo[1,2-b][1,2,4]triazin-2-yl)benzamide, ruxolitinib, panobinostat, osilodrostat, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide, (S)—N—((S)-1-cyclohexyl-2-((S)-2-(4-(4-fluorobenzoyl)thiazol-2-yl)pyrrolidin-1-yl)-2-oxoethyl)-2-(methylamino)propanamide,sonidegib phosphate, ceritinib, 7-cyclopentyl-N,N-dimethyl-2-((5-(piperazin-1-yl)pyridin-2-yl)amino)-7H-pyrrolo[2,3-d]pyrimidine-6-carboxamide, N-(4-((1R,3S,5S)-3-amino-5-methylcyclohexyl)pyridin-3-yl)-6-(2,6-difluorophenyl)-5-fluoropicolinamide, 2-(2',3-dimethyl-[2,4'-bipyridin]-5-yl)-N-(5-(pyrazin-2-yl)pyridin-2-yl)acetamide,encorafenib, 7-cyclopentyl-N,N-dimethyl-2-((5-((1R,6S)-9-methyl-4-oxo-3,9-diazabicyclo[4.2.1]-nonan-3-yl)pyridin-2-yl)amino)-7H-pyrrolo[2,3-d]pyrimidine-6-carboxamide, binime-tinib, everolimus, 1-methyl-5-((2-(5-(trifluoromethyl)-1H-imidazol-2-yl)pyridin-4-yl)oxy)-N-(4-(trifluoromethyl)phenyl)-1H-benzo[d]imidazol 2-amine, pasi-reotide diaspartate, dovitinib, (R,E)-N-(7-chloro-1-(1-(4-(dimethylamino)but-2-enoyl)azepan-3-yl)-1H-benzo[d]imidazol-2-yl)-2-methylisonicotinamide, N6-(2-isopropoxy-5-methyl-4-(1-methylpiperidin-4-yl)phenyl)-N4-(2-(isopropylsulfonyl)-phenyl)-1H-pyrazolo[3,4-d]pyrimidine-4,6-diamine, 3-(4-(4-((5-chloro-4-((5-methyl-1H-pyrazol-3-yl)amino)pyrimidin-2-yl)amino)-5-fluoro-2-methylphenyl)piperidin-1-yl)thietane 1,1-dioxide, 5-chloro-N2-(2-fluoro-5-methyl-4-(1-(tetrahydro-2H-pyran-4-yl)piperidin-4-yl)phenyl)-N4-(5-methyl-1H-pyrazol-3-yl)pyrimidine-2,4-diamine, 5-chloro-N2-(4-(1-ethylpiperidin-4-yl)-2-fluoro-5-methylphenyl)-N4-(5-methyl-1H-pyrazol-3-yl)pyrimidine-2,4-diamine, valspodar, and vatalanib succinate.

In other embodiments, the compounds of the present invention can be used in combination with a PKC inhibitor, a BCR-ABL inhibitor, an HSP90 inhibitor, an inhibitor of PI3K and/or mTOR, an FGFR inhibitor, a PI3K inhibitor, an FGFR inhibitor, a PI3K inhibitor, an inhibitor of cytochrome P450 (e.g., a CYP17 inhibitor), a HDM2 inhibitor, an aromatase inhibitor, an inhibitor of p53 and/or a p53/Mdm2 interaction, or a CSF-1R tyrosine kinase inhibitor.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

The dosage for the combination partners mentioned above is usually 1/5 of the lowest dose normally recommended up to 1/1 of the normally recommended dose.

In yet another aspect the present invention relates a method for treating a disease or condition associated with or modulated by, or which can be influenced by the modulation of STING in a patient, said method includes the step of administering to the patient, preferably a human, in need of such treatment a therapeutically effective amount of a compound of the present invention in combination with a therapeutically effective amount of one or more additional therapeutic agents described in hereinbefore.

The use of the compound according to the invention in combination with the additional therapeutic agent may take place simultaneously or at staggered times.

The compound according to the invention and the one or more additional therapeutic agents may both be present together in one formulation or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

Synthesis of Compounds According to the Present Invention

General Technical Remarks

The terms "ambient temperature" and "room temperature" are used interchangeably and designate a temperature of about 20° C., e.g. 15 to 25° C.

As a rule, $^1$H NMR spectra and/or mass spectra have been obtained of the compounds prepared. Unless otherwise stated, all chromatographic operations were performed at room temperature. During cyclic dinucleotide synthesis, evaporation of solvents was typically performed by rotary evaporation under reduced pressure with water bath temperatures not exceeding 35° C. Furthermore, during cyclic dinucleotide synthesis, reactions were performed under nitrogen or argon.

Nuclear magnetic resonance (NMR) spectra: For $^1$H spectra, chemical shifts were referenced to the DMSO solvent signal (2.50 ppm) or, for measurements in $D_2O$, to DSS (4,4-dimethyl-4-silapentane-1-sulfonic acid). The $^{31}$P NMR spectra were indirectly referenced by comparison of the absolute frequencies of $^1$H/$^{31}$P (Bruker BioSpin GmbH, Software: TopSpin, au program: xsi). All $^{31}$P NMR spectra were recorded with proton decoupling.

LIST OF ABBREVIATIONS

ACN acetonitrile
aq. aqueous
° C. degree Celsius
DA diode array
DBU diazabicyclo[5.4.0]undec-7-ene
CEP (2-cyanoethyl)-(N,N-diisopropyl)]-phosphoramidite
DCM dichloromethane
DDTT 3-((N,N-dimethyl-aminomethylidene)amino)-3H-1,2,4-dithiazole-3-thione
DIPEA diisopropylethylamine
DMAP 4-dimethylaminopyridine
DMF N,N-dimethylformamide
DMOCP 2-chloro-5,5-dimethyl-2-oxo-1,3,2-dioxaphosphorinane
DMT 4,4'-dimethoxytrityl
ESI-MS electrospray ionisation mass spectrometry
EtOAc ethyl acetate
eq equivalent FC flash-chromatography, SiO$_2$ is used if no further details given
h hour
HCl hydrogenchloride
HATU [dimethylamino-(1,2,3-triazolo[4,5-b]pyridin-3-yloxy)-methylene]-dimethyl-ammonium hexafluorophosphate
HPLC high performance liquid chromatography
L liter
LiHMDS lithium Hexamethyldisilazide
m/z mass-to-charge ratio
MeOH methanol
min minute
mL milliliter
MS mass spectrum
n.d. not determined
NH$_4$OH solution of NH$_3$ in water
Pd-PEPPSI-IPent™ dichloro[1,3-bis(2,6-Di-3-pentylphenyl)imidazol-2-ylidene](3-chloropyridyl)palladium(II)
psi pound per square inch
RT room temperature (about 20° C.)
SEM 2-(trimethylsilyl)ethoxymethyl
Sol solvent
TBS tert-butyl-dimethylsilyl
TEA triethyl amine
TEAF triethylammonium formate
TF/TFA trifluoroacetic acid
TFAA trifluoroacetic acid anhydride
THF tetrahydrofuran
t$_R$ retention time in minutes Analytical HPLC-configurations:
Configuration A (qradient HPLC):
VWR/Hitachi: L-2130 Pump; VWR/Hitachi: L-2200 Autosampler; VWR/Hitachi: L-2350 Column Oven (set at 30° C.); VWR/Hitachi: L-2400 variable wavelength UV/Vis detector; EZChrom software version 3.3.1 SP1.
YMC*GEL ODS-A 12 nm (10 μm; 250×0.4 mm)) channel A=20 mM TEAF (pH 6.8) in water; channel B=100% acetonitrile, 20 mM TEAF (pH 6.8). Gradient: 0 min 100% A; 30 min 100% B; 40 min 100% B, 30° C.; flow rate: 1.0 mL/min; UV 261 nm;
Configuration B (Isocratic HPLC):
VWR/Hitachi: L-7100 Pump; VWR/Hitachi: L-7400 variable wavelength UV/Vis detector; VWR/Hitachi: D-7500 Integrator.
Analytical HPLC (configuration C; YMC*GEL ODS-A 12 nm (10 μm; 250×0.4 mm)) 11% acetonitrile, 20 mM TEAF (pH 6.8) in water; flow rate: 1.0 mL/min; UV 264 nm;
LC-MS-Analytics:
HPLC-System: VWR/Hitachi: L-2130 Pump; VWR/Hitachi: L-2200 Autosampler; VWR/Hitachi: L-2300 Column Oven; VWR/Hitachi: L-2450 Diode Array Detector; Agilent: OpenLab
MS-System: Bruker Esquire LC 6000 spectrometer
System A
Column: Kromasil 100-5 C$_8$, 5 μm, 50 mm×3 mm.
Flow rate: 0.4 mL/min, 35° C., UV-detection range: 220-300 nm
Mass spectrum: Recorded on a mass spectrometer using negative and positive electrospray ionization
Solvents: A: acetonitrile
B: water
C: 20 mM NH$_4$HCO$_3$ (pH 7) in water
Gradient:

| Time | A % | B % | C % |
| --- | --- | --- | --- |
| 0 | 20 | 75 | 5 |
| 20 | 95 | 0 | 5 |
| 23 | 95 | 0 | 5 |
| 24 | 20 | 75 | 5 |
| 30 | 20 | 75 | 5 |

Sample preparation: Samples (2 μL-10 μL) were dissolved in 175 μL acetonitrile and 175 μL water, injection volume 2 μL-10 μL.
System B
Column: ACE 3 AQ 110-3 C$_{18}$, 5 μm, 50 mm×3 mm.
Flow rate: 0.4 mL/min, 35° C., UV-detection range: 220-300 nm
Mass spectrum: Recorded on a mass spectrometer using negative and positive electrospray ionization
Solvents: A: acetonitrile
B: water
C: 20 mM NH$_4$HCO$_3$ (pH 7) in water
Gradient:

| Time | A % | B % | C % |
| --- | --- | --- | --- |
| 0 | 2 | 93 | 5 |
| 20 | 60 | 35 | 5 |
| 23 | 95 | 0 | 5 |
| 24 | 2 | 93 | 5 |
| 30 | 2 | 93 | 5 |

| Device Supplier: | Agilent |
| --- | --- |
| Description: | Agilent 1200 with DA- and MS-Detector |
| Method Name: | SYSTEM C |
| Column: | Sunfire, 3 × 30 mm, 2.5 μm |
| Column Supplier: | Waters |

| Gradient/ Solvent Time [min] | % Sol [H2O, 0.1% TFA] | % Sol [Acetonitril] | Flow [ml/min] | Temp [° C.] |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |

| Device Supplier: | Agilent |
| --- | --- |
| Description: | Agilent 1200 with DA- and MS-Detector |
| Method Name: | SYSTEM C |

| 1.25 | 0 | 100 | 3 | 60 |
| --- | --- | --- | --- | --- |
| 1.40 | 0 | 100 | 3 | 60 |

| Device Supplier: | Agilent |
| --- | --- |
| Description: | Agilent 1200 with DA- and MS-Detector |
| Method Name: | SYSTEM D |
| Column: | XBridge C18, 3 × 30 mm, 2.5 μm |
| Column Supplier: | Waters |

| Gradient/ Solvent Time [min] | % Sol [H2O, 0.1% NH3] | % Sol [Acetonitril] | Flow [ml/min] | [° C.] Temp |
| --- | --- | --- | --- | --- |
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| Device Supplier: | Agilent |
| --- | --- |
| Description: | Agilent 1200 with DA- and MS-Detector |
| Method Name: | System E |
| Column: | Stable Bond, 3 × 30 mm, 1.8 μm |
| Column Supplier: | Agilent |

| Gradient/ Solvent Time [min] | % Sol [H2O, 0.1% TFA] | % Sol [Acetonitril] | Flow [ml/min] | Temp [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

| | |
|---|---|
| Device Supplier: | Agilent |
| Description: | Agilent 1200 with DA- and MS-Detector |
| Method Name: | System F |
| Column: | Nucleodur SiOH, 3 × 30 mm, 5.0 µm |
| Column Supplier: | Macherey-Nagel |

| Gradient/ Solvent Time [min] | % Sol DCM | % Sol MeOH | Flow [ml/min] | Temp [° C.] |
|---|---|---|---|---|
| 0.00 | 100 | 0 | 2.5 | 30 |
| 0.60 | 100 | 0 | 2.5 | 30 |
| 1.80 | 95 | 5 | 2.5 | 30 |
| 2.60 | 75 | 25 | 2.5 | 30 |
| 3.00 | 50 | 50 | 2.5 | 30 |
| 3.10 | 0 | 100 | 2.5 | 30 |
| 3.50 | 0 | 100 | 2.5 | 30 |
| 3.55 | 100 | 0 | 2.5 | 30 |
| 3.80 | 100 | 0 | 2.5 | 30 |
| 5.00 | 100 | 0 | 3.0 | 30 |
| 5.20 | 100 | 0 | 3.0 | 30 |

SYNTHESES OF INTERMEDIATES

Intermediate 1.1

Imidazopyridazinon-β-D-ribofuranoside (1-(β-D-ribofuranosyl)imidazo[4,5-d]pyridazin-4(5H)-one)

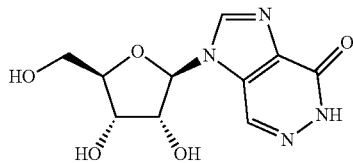 [SMILES: O=c1[nH]ncc2c1ncn2[C@@H]1O[C@H](CO)[C@@H](O)[C@H]1O]

The title compound was prepared as described in *J. Chem. Soc. Perkin Trans.* 1 1989, 1769-1774.

Intermediate 1.2

5'-DMT-imidazopyridazinon-β-D-ribofuranoside

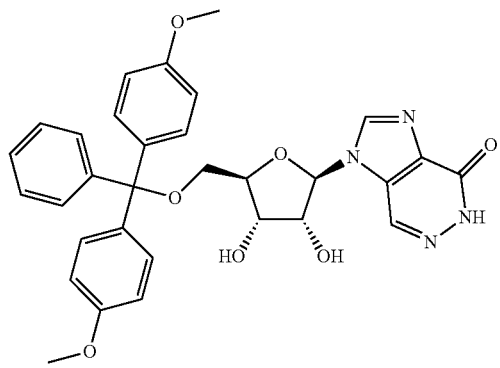 [SMILES: COc1ccc(C(OC[C@H]2O[C@@H](n3cnc4c(=O)[nH]ncc43)[C@H](O)[C@@H]2O)(c2ccccc2)c2ccc(OC)cc2)cc1]

Imidazopyridazinon-β-D-ribofuranoside (INTERMEDIATE 1.1, 4.00 g, 14.9 mmol) was azeotroped with anhydrous pyridine (3×20 mL), dried in vacuo and dissolved in anhydrous pyridine (25 mL). To this solution was added a solution of 4,4'-dimethoxytrityl chloride (5.05 g, 14.9 mmol) in anhydrous pyridine (15 mL) and the reaction mixture was stirred for 1 h at room temperature. The reaction mixture was evaporated under reduced pressure and the resulting residue was purified by preparative reversed phase HPLC (X-Bridge C18, acetonitrile/water/NH₃)

LC-MS (system D):

$t_{Ret}$=0.82 min; ESI-MS: 571 [M+H]⁺

Intermediate 1.3-a and Intermediate 1.3-b

5'-DMT-2'-TBS-imidazopyridazinon-β-D-ribofuranoside (Intermediate 1.3-a) and 5'-DMT-3'-TBS-imidazopyridazinon-β-D-ribofuranoside (Intermediate 1.3-b)

INTERMEDIATE 1.3-a

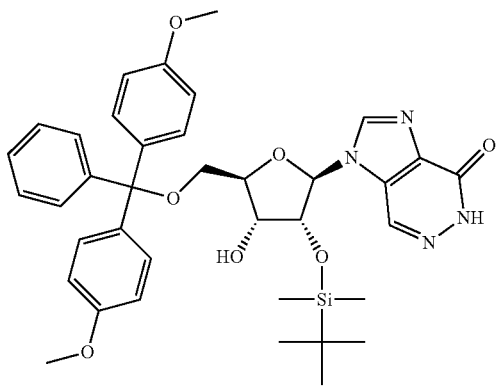

INTERMEDIATE 1.3-b

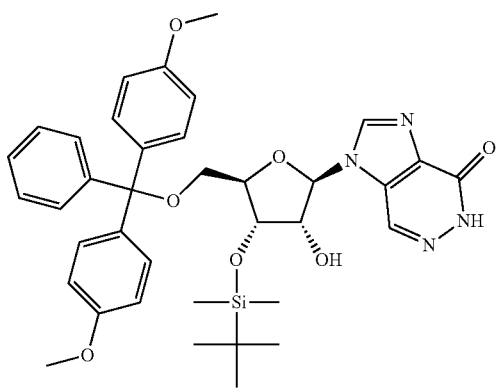

5'-DMT-imidazopyridazinon-β-D-ribofuranoside (INTERMEDIATE 1.2, 5.30 g, 9.29 mmol) was azeotroped with anhydrous pyridine (3×30 mL), dried in vacuo and dissolved in anhydrous pyridine (20 mL). To this solution was added imidazole (1.90 g, 27.9 mmol) and tert-butylchlorodimethylsilane (1.54 g, 10.2 mmol) and the reaction mixture was stirred for 6 h at room temperature. The reaction mixture was partitioned between dichloromethane and water. The organic layer was separated and the aqueous layer extracted with dichloromethane. The combined organic extracts were washed with brine, dried using a hydrophobic frit and evaporated under reduced pressure. The resulting residue was purified by mid-pressure column chromatography (silica gel, gradient of 5-20% acetone in dichloromethane).

LC-MS (system F):
INTERMEDIATE 1.3-a: $t_{Ret}$=1.57 min; ESI-MS: 685 [M+H]$^+$
INTERMEDIATE 1.3-b: $t_{Ret}$=1.67 min; ESI-MS: 685 [M+H]$^+$ Intermediate 1.4

5'-DMT-3'-TBS-2'-CEP-imidazopyridazinon-β-D-ribofuranoside

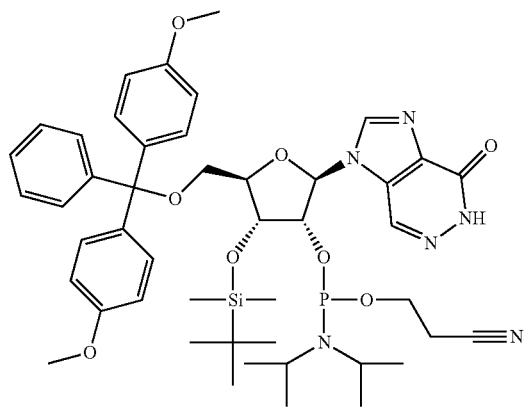 [SMILES: COc1ccc(C(OC[C@H]2O[C@@H](n3cnc4c(=O)[nH]ncc43)[C@H](OP(OCCC#N)N(C(C)C)C(C)C)[C@@H]2O[Si](C)(C)C(C)(C)C)(c2ccccc2)c2ccc(OC)cc2)cc1]

5'-DMT-3'-TBS-imidazopyridazinon-β-D-ribofuranoside (INTERMEDIATE 1.3-b, 1.75 g, 2.56 mmol) was azeotroped with anhydrous acetonitrile (3×25 mL), dried in vacuo and dissolved in anhydrous dichloromethane (45 mL). To this solution was added 2-cyanoethyl N,N,N',N'-tetraisopropylphosphorodiamidite (1.62 mL, 5.12 mmol) and tetrazole (5.69 mL of a 0.5 M solution in acetonitrile, 2.85 mmol) and the reaction mixture was stirred at room temperature for 4 h. The reaction mixture was diluted with dichloromethane and washed with aqueous sodium hydrogen carbonate solution. The organic layer was separated and the aqueous layer was extracted with dichloromethane. The combined organic extracts were dried using a hydrophobic frit and evaporated under reduced pressure. The resulting residue was purified by mid-pressure column chromatography (silica gel (deactivated with triethylamine in dichloromethane), gradient of 20-100% ethyl acetate (3% triethylamine) in cyclohexane). The product was obtained as a mixture of diastereoismers.
LC-MS (system D):
$t_{Ret}$=1.33 min; ESI-MS: 885 [M+H]$^+$
$^{31}$P NMR (162 MHz, 303 K, CDCl$_3$) δ 150.9 and 149.7 ppm.

Intermediate 1.5

5'-OH-2'-TBS-3'-H-phosphonate-N$^6$-Bz-adenosine

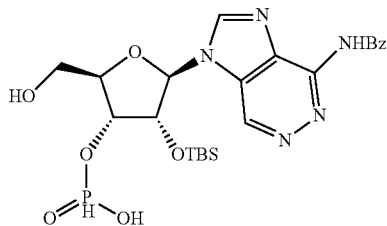

N$^6$-Bz-5'-DMT-2'-TBS-3'-CEP-adenosine (obtained from ChemGenes, 0.890 g, 0.90 mmol) was dissolved in acetonitrile (15 mL) and water (0.033 mL, 1.83 mmol, 2 eq.) at room temperature. Pyridinium trifluoroacetate (0.210 g, 1.09 mmol, 1.2 eq.) was added and the reaction mixture was stirred at room temperature for 10 minutes. tert-Butylamine (10 mL, 95.7 mmol) was added and the reaction mixture was stirred at room temperature for 30 minutes. The reaction mixture was evaporated under reduced pressure, re-dissolved in anhydrous acetonitrile (25 mL) and evaporated under reduced pressure to yield a white to colorless foam. The residue was dissolved in dichloromethane (25 mL) and water (0.162 mL, 9 mmol, 10 eq.). Dichloroacetic acid (0.670 mL, 8.12 mmol, 9 eq.) in dichloromethane (25 mL) was added and the resulting orange solution was stirred at room temperature for 10 minutes. Pyridine (1.31 mL, 16.23 mmol, 18 eq.) was added and the reaction mixture was stirred at room temperature for 5 minutes.
LC-MS analytics of the raw material confirmed the presence of INTERMEDIATE 1.5.
LC-MS (system A):
$t_{Ret}$=3.10 min; ESI-MS: 550 [M+H]$^+$
The flask was stoppered, carefully sealed and stored at +2° C. for 16 hours. The solvents were evaporated under reduced pressure and the residue was azeotroped with anhydrous acetonitrile (4×15 mL). During the last evaporation procedure the solution was concentrated to approximately 5 mL of final azeotrope. The resulting anhydrous solution of intermediate 1.5 was immediately used in the next sequence of reactions.

Intermediate 1.6

Linear Dimer 5'-OH-3'-TBS-imidazopyridazinon-β-D-ribofuranoside-(2'→5')-cyanoethyl-phosphorothioate-2'-TBS-3'-H-phosphonate-N$^6$-Bz-adenosine

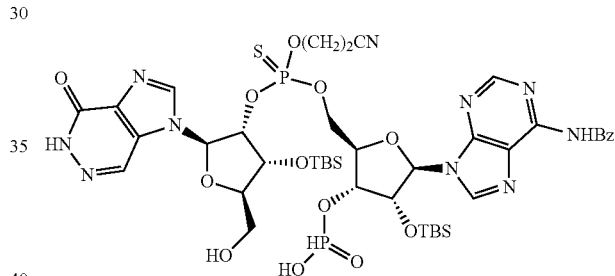

5'-DMT-3'-TBS-2'-CEP-imidazopyridazinon-β-D-ribofuranoside (INTERMEDIATE 1.4, 1.340 g, 1.51 mmol, 1.7 eq.) was azeotroped with anhydrous acetonitrile (4×10 mL). During the last evaporation procedure the solution was concentrated to approximately 3 mL of the final azeotrope. The resulting solution was added to 5'-OH-2'-TBS-3'-H-phosphonate-N$^6$-Bz-adenosine (INTERMEDIATE 1.5) dissolved in approximately 5 mL anhydrous acetonitrile (theoretical amount of desired material: 0.495 g, 0.90 mmol) at room temperature. The reaction mixture was stirred at room temperature for 30 minutes. ((N,N-dimethylamino-methylidene)amino)-3H-1,2,4-dithiazoline-3-thione (DDTT) (0.203 g, 0.99 mmol, 1.1 eq.) was added and the reaction mixture was stirred at room temperature for 30 minutes. The volatiles were evaporated under reduced pressure and the residue was dissolved in dichloromethane (25 mL) and water (0.162 mL, 9 mmol, 10 eq.). Dichloroacetic acid (1.340 mL, 16.24 mmol, 18 eq.) in dichloromethane (25 mL), was added and the orange solution was stirred at room temperature for 20 minutes. Pyridine (10 mL) was added and the reaction mixture was stirred at room temperature for 5 minutes. LC-MS analytics of the raw material confirmed the presence of INTERMEDIATE 1.6 as a mixture of diastereoisomers.
LC-MS (system A):
INTERMEDIATE 1.6-a: $t_{Ret}$=7.36 min; INTERMEDIATE 1.6-b: $t_{Ret}$=7.57 min;
ESI-MS: 1063 [M+H]$^+$ for each diastereoisomer.

The flask was stoppered, carefully sealed and stored at +2° C. for 16 hours. The mixture was evaporated under reduced pressure and the residue was co-evaporated with anhydrous pyridine (2×20 mL) under reduced pressure. A further portion of 40 mL anhydrous pyridine was added and the residue was concentrated under reduced pressure to approximately 20 mL total volume. The resulting anhydrous solution of INTERMEDIATE 1.6 was immediately used in the next sequence of reactions.

Intermediate 1.7

Cyclic Dimer 3'-TBS-imidazopyridazinon-β-D-ribo-furanoside-(2'→5')-cyanoethyl-phosphorothioate-2'-TBS-$N^6$-Bz-adenosine-(3'→5')-phosphorothioate

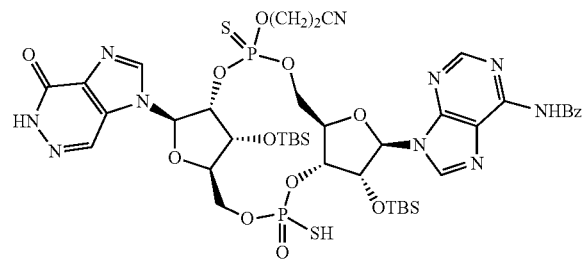

2-Chloro-5,5-dimethyl-1,3,2-dioxaphosphorinane 2-oxide (DMOCP) (0.581 g, 3.15 mmol, 3.5 eq.) was added to crude 5'-OH-3'-TBS-imidazopyridazinon-β-D-ribofuranoside-(2'→5')-CE-PS-2'-TBS-3'-H-phosphonate-$N^6$-Bz-adenosine (INTERMEDIATE 1.6) (theoretical amount of desired material in crude preparation: 0.957 g, 0.90 mmol) in anhydrous pyridine in a total volume of approximately 20 mL. The resulting mixture was stirred at room temperature for 20 minutes. Water (0.570 mL, 31.6 mmol, 35.1 eq.) and 3H-1,2-benzodithiol-3-one (0.230 g, 1.37 mmol, 1.5 eq.) were added and stirring was continued at room temperature. After 20 minutes, the reaction mixture was poured into a solution of sodium hydrogen carbonate (4.500 g, 53.6 mmol) in 150 mL water and was shaken at room temperature for 5 minutes, followed by the addition of a mixture of ethyl acetate/methyl-tert-butylether (150 mL, 1:1). The organic phase was separated and the aqueous phase was further extracted two times with ethyl acetate/methyl-tert-butylether (2×75 mL, 1:1). The combined organic phases were dried with anhydrous magnesium sulfate, followed by evaporation of solvents under reduced pressure and a final co-evaporation with 100 mL anhydrous toluene. The raw material was purified by preparative flash chromatography (160 g silica gel, gradient of 0-12.5% MeOH in dichloromethane) to yield 0.78 g of purity enriched INTERMEDIATE 1.7 (mixture of diastereomers).

LC-MS (system A):
INTERMEDIATE 1.7-a: $t_{Ret}$=7.56 min; INTERMEDIATE 1.7-b: $t_{Ret}$=8.18 min;
INTERMEDIATE 1.7-c: $t_{Ret}$=9.02 min; INTERMEDIATE 1.7-d: $t_{Ret}$=10.17 min;
ESI-MS: 1077 [M+H]$^+$ for each diastereoisomer.

Intermediate 1.8

Cyclic Dimer 3'-TBS-imidazopyridazinon-β-D-ribofuranoside-(2'→5')-phosphorothioate-2'-TBS-adenosine-(3'→5')-phosphorothioate

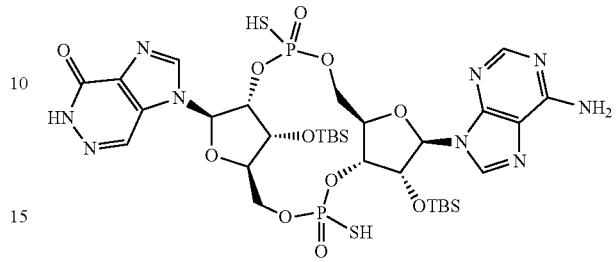

125 mL 33% methylamine in absolute ethanol was added to purity enriched 3'-TBS-imidazopyridazinon-β-D-ribofuranoside-(2'→5')-cyanoethyl-phosphorothioate-2'-TBS-$N^6$-Bz-adenosine-(3'→5')-phosphorothioate (INTERMEDIATE 1.7; 0.780 g) and the resulting solution was stirred at room temperature for 4 hours. All volatiles were evaporated under reduced pressure and further dried in vacuo yielding 0.758 g crude INTERMEDIATE 1.8 (mixture of diastereomers), which was directly used in the next reaction.

LC-MS (system A):
INTERMEDIATE 1.8-a: $t_{Ret}$=1.47 min; INTERMEDIATE 1.8-b: $t_{Ret}$=3.60 min;
INTERMEDIATE 1.8-c: $t_{Ret}$=3.90 min; INTERMEDIATE 1.8-d: $t_{Ret}$=5.53 min;
ESI-MS: 920 [M+H]$^+$ for each diastereoisomer.

Intermediate 2.1

5'-OH-2'-F-3'-H-phosphonate-$N^6$-Bz-2'-deoxyadenosine

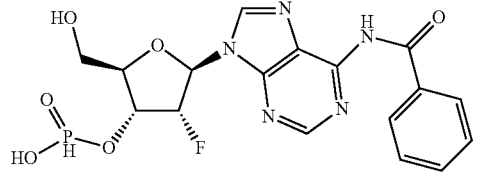

$N^6$-Benzoyl-5'-DMT-2'-F-2'-deoxyadenosine-3'-CEP (obtained from Alfa Aesar) (1.05 g, 1.20 mmol) was dissolved in acetonitrile (6 mL) and water (0.043 mL, 2.40 mmol, 2 eq.) at room temperature. Pyridinium trifluoroacetate (278 mg, 1.44 mmol, 1.2 eq.) was added and the reaction mixture was stirred at room temperature for 5 minutes. Afterwards, tert-butylamine (6.0 mL, 57.1 mmol) was added and the reaction mixture was stirred at room temperature for 15 minutes. The reaction mixture was evaporated in vacuo, re-dissolved (2×) in anhydrous acetonitrile (12 mL) and again evaporated in vacuo to yield a white to colorless foam. The residue was dissolved in dichloromethane (14.4 mL) and water (0.22 mL, 12.0 mmol, 10 eq.). Dichloroacetic acid in dichloromethane (6%, 14.4 mL) was added and the resulting orange solution was stirred at room temperature for 10 minutes. Pyridine (1.64 mL, 20.3 mmol, 17 eq.) was added and the reaction mixture was evaporated in vacuo and azeotroped with anhydrous acetonitrile (3×11 mL). Finally the remaining crude product was dried in high vacuo for additional 30 min and used without further purification.

LC-MS analytics of the raw material confirmed the presence of INTERMEDIATE 2.1.
LC-MS (system E):
$t_{Ret}$=0.64 min ESI-MS: 438 [M+H]$^+$.

Intermediate 2.2

Linear Dimer 5'-OH-3'-TBS-imidazopyridazinon-β-D-ribofuranoside-(2'→5')-cyanoethyl-phosphorothioate-2'-F-3'-H-phosphonate-N⁶-Bz-2'-deoxyadenosine

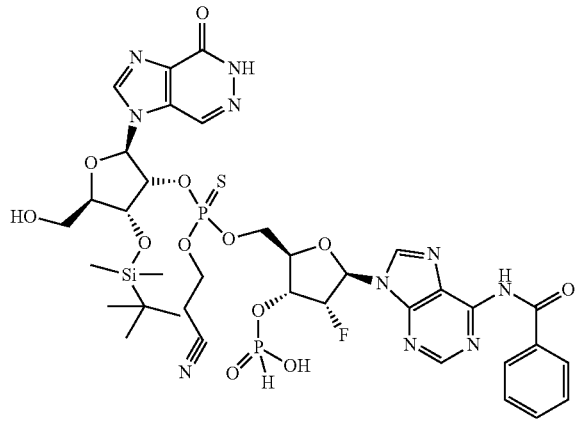

5'-DMT-3'-TBS-2'-CEP-imidazopyridazinon-β-D-ribofuranoside (INTERMEDIATE 1.4, 1.38 g, 1.56 mmol, 1.0 eq.) was dissolved in anhydrous acetonitrile (10 mL) and was azeotropically evaporated in vacuo. This operation was repeated another three times leaving about 5 mL of azeotrope in the flask at the last evaporation. 10 pieces of molecular sieve (3 Å) were added and the resulting mixture was added to 5'-OH-2'-F-3'-H-phosphonate-N⁶-Bz-2'-deoxyadenosine (INTERMEDIATE 2.1) dissolved in approximately 3 mL anhydrous acetonitrile (theoretical amount of desired material: 523 mg, 1.20 mmol) at room temperature. The reaction mixture was stirred at room temperature for 5 minutes. ((N,N-dimethylamino-methylidene)amino)-3H-1,2,4-dithiazoline-3-thione (DDTT) (275 mg, 1.34 mmol, 0.9 eq.) was added and the reaction mixture was stirred at room temperature for 30 minutes. The volatiles were evaporated in vacuo and the residue was dissolved in dichloromethane (20 mL) and water (0.216 mL, 12 mmol, 7.7 eq.). Dichloroacetic acid in dichloromethane (6%, 19.2 mL) was added and the resulting orange solution was stirred at room temperature for 10 minutes. After this period, pyridine (12 mL) was added and the reaction mixture was evaporated in vacuo. Finally the remaining crude product was dried in high vacuo for additional 30 min and used without further purification and characterization.

Intermediate 2.3

Cyclic Dimer 3'-TBS-imidazopyridazinon-β-D-ribofuranoside-(2'→5')-cyanoethyl-phosphorothioate-2'-F—N⁶-Bz-2'-deoxyadenosine-(3'→5')-phosphorothioate

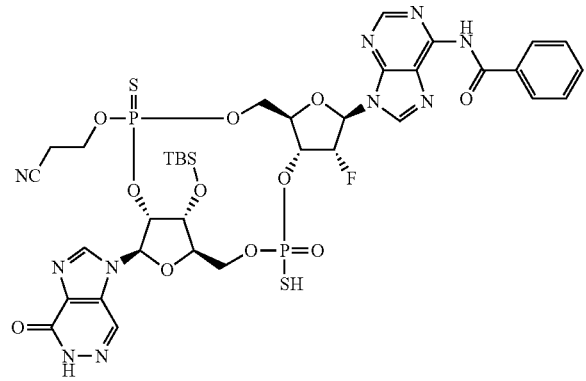

Crude intermediate 2.2 (maximum theoretical amount of desired material: 1.48 g, 1.56 mmol) was dissolved in 36 mL anhydrous pyridine and reduced to approximately 20 mL in vacuo. 2-Chloro-5,5-dimethyl-1,3,2-dioxaphosphorinane 2-oxide (DMOCP) (775 mg, 4.20 mmol, 2.7 eq.) was added and the resulting mixture was stirred at room temperature for 5 minutes. Water (0.75 mL, 41.3 mmol, 26.5 eq.) and 3H-1,2-Benzodithiol-3-one (0.302 g, 1.80 mmol, 1.15 eq.) were added and stirring was continued at room temperature. After 5 minutes, the reaction mixture was poured into a solution of sodium hydrogen carbonate (4.00 g, 47.6 mmol) in 140 mL water and was stirred at room temperature for 5 minutes, followed by the addition of a mixture of ethyl acetate/methyl-tert-butylether (140 mL, 1:1). The organic phase was separated and the aqueous phase was further extracted with ethyl acetate/methyl-tert-butylether (1:1). The organic phases were combined and the solvent was removed in vacuo.

The remaining residue was dissolved in a minimum volume of dichloromethane and purified by preparative flash chromatography (silica gel, DCM/MeOH: 100/0→80/20). Product-containing fractions were analyzed by HPLC-MS. Product-containing fractions were combined and the solvent removed in vacuo to yield 900 mg of a mixture of diastereoisomers. LC-MS analytics of the material confirmed the presence of INTERMEDIATEs 2.3-a/b/c/d.

LC-MS (system E):
INTERMEDIATE 2.3-a: $t_{Ret}$=0.95 min; INTERMEDIATE 2.3-b: $t_{Ret}$=0.98 min;
INTERMEDIATE 2.3-c: $t_{Ret}$=1.00 min; INTERMEDIATE 2.3-d: $t_{Ret}$=1.03 min;
ESI-MS: 965 [M+H]⁺ for each diastereoisomer.

Intermediate 2.4

Cyclic Dimer 3'-TBS-imidazopyridazinon-β-D-ribofuranoside-(2'→5')-phosphorothioate-2'-F-2'-deoxyadenosine-(3'→5')-phosphorothioate

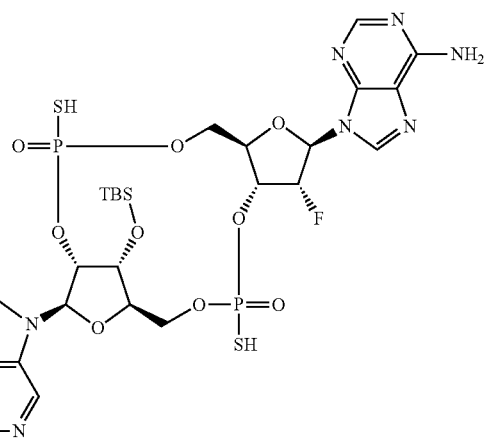

To 10 mL methanol and 10 mL aq. ammonia (30-33%) were added 300 mg (max. theoretical amount of desired material: 0.31 mmol) of INTERMEDIATE 2.3. The resulting mixture was stirred at 50° C. for 15 h. The reaction mixture was cooled to room temperature and nitrogen was bubbled through the mixture for 30 min. The solvent was removed in vacuo, the mixture re-dissolved in anhydrous acetonitrile (30 mL) and again evaporated in vacuo. The residue was triturated with anhydrous acetonitrile, filtered, washed with 5 ml ACN and dried over night at room temperature. The crude product was dissolved in DMF and purified by preparative HPLC (X-Bridge C-18; acetonitrile/ $H_2O/NH_3$). Product-containing fractions were collected and the solvent was removed by lyophilization. By this method, all four diastereoisomers could be separated.

LC-MS analytics of the material confirmed the presence of INTERMEDIATEs 2.4-a/b/c/d.
LC-MS (system C):
INTERMEDIATE 2.4-a: $t_{Ret}$=1.04 min; INTERMEDIATE 2.4-b: $t_{Ret}$=1.10 min;
INTERMEDIATE 2.4-c: $t_{Ret}$=1.13 min; INTERMEDIATE 2.4-d: $t_{Ret}$=1.15 min;
ESI-MS: 808 [M+H]$^+$ for each diastereoisomer.

Intermediate 3.1

5'-OH-3'-H-phosphonate-$N^6$-Bz-LNA-adenine

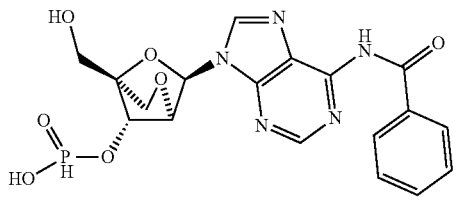

INTERMEDIATE 3.1 was prepared analogously to INTERMEDIATE 2.1 by using "LNA-A amidite" (EQ-0063-1000, obtained from Exiqon) as starting material.

LC-MS analytics of the raw material confirmed the presence of INTERMEDIATE 3.1.
LC-MS (system E):
$t_{Ret}$=0.63 min; ESI-MS: 448 [M+H]$^+$ Intermediate 3.2

Linear Dimer 5'-OH-3'-TBS-imidazopyridazinon-β-D-ribofuranoside-(2'→5')-cyanoethyl-phosphorothioate-3'-H-phosphonate-$N^6$-Bz-LNA-adenine

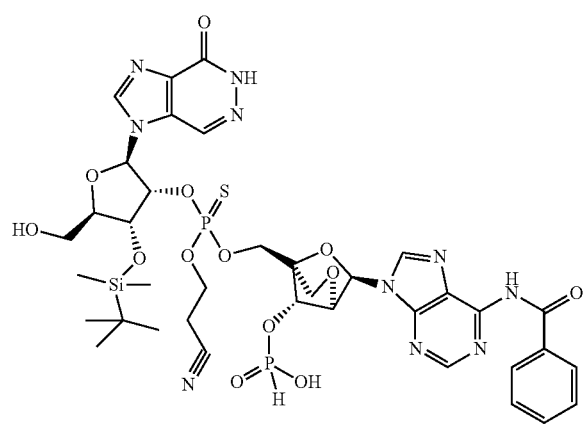

INTERMEDIATE 3.2 was prepared analogously to INTERMEDIATE 2.2 by using INTERMEDIATE 3.1 and INTERMEDIATE 1.4 as starting materials.

Intermediate 3.3

Cyclic Dimer 3'-TBS-imidazopyridazinon-β-D-ribofuranoside-(2'→5')-cyanoethyl-phosphoro-thioate-$N^6$-Bz-LNA-adenine-(3'→5')-phosphorothioate

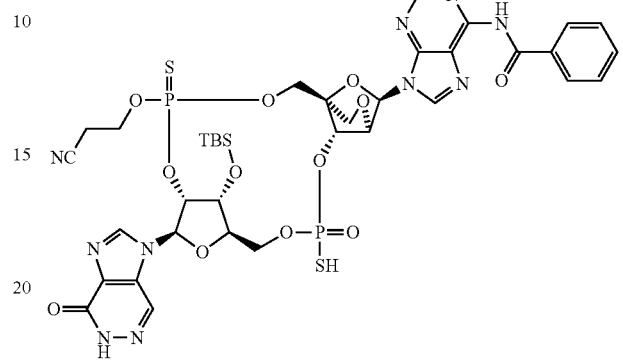

INTERMEDIATE 3.3 was prepared analogously to INTERMEDIATE 2.3 by using INTERMEDIATE 3.2 as starting material.

LC-MS analytics of the material confirmed the presence of INTERMEDIATEs 3.3-a/b/c/d.
LC-MS (system E):
INTERMEDIATE 3.3-a: $t_{Ret}$=0.94 min; INTERMEDIATE 3.3-b: $t_{Ret}$=0.98 min;
INTERMEDIATE 3.3-c: $t_{Ret}$=0.99 min; INTERMEDIATE 3.3-d: $t_{Ret}$=1.03 min;
ESI-MS: 975 [M+H]$^+$ for each diastereoisomer.

Intermediate 3.4

Cyclic Dimer 3'-TBS-imidazopyridazinon-β-D-ribofuranoside-(2'→5')-phosphorothioate-LNA-adenine-(3'→5')-phosphorothioate

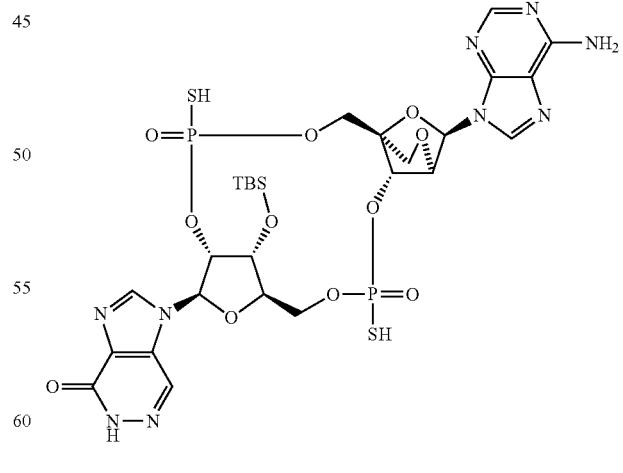

INTERMEDIATE 3.4 was prepared analogously to INTERMEDIATE 2.4 by using INTERMEDIATE 3.3 as starting material.

LC-MS analytics of the material confirmed the presence of INTERMEDIATEs 3.4-a/b/c/d.

LC-MS (system C):
INTERMEDIATE 3.4-a: $t_{Ret}$=0.81 min; INTERMEDIATE 3.4-b: $t_{Ret}$=0.89 min;
INTERMEDIATE 3.4-c: $t_{Ret}$=0.91 min; INTERMEDIATE 3.4-d: $t_{Ret}$=0.99 min;
ESI-MS: 818 [M+H]$^+$ for each diastereoisomer.

Intermediate 4.1

5'-OH-2'-TBS-3'-H-phosphonate-purine-β-D-ribofuranoside

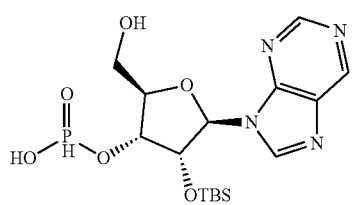

INTERMEDIATE 4.1 was prepared analogously to INTERMEDIATE 1.5 by using 5'-DMT-2'-TBS-3'-CEP-purine-β-D-ribofuranoside as starting material which can be prepared as described in Fu et al. Biochemistry 1993, 32, 10629-10637. In contrast to INTERMEDIATE 1.5 this intermediate was not stored overnight but used immediately in the next sequence of reactions.

LC-MS analytics of the raw material confirmed the presence of INTERMEDIATE 4.1.
LC-MS (system B):
$t_{Ret}$=8.56 min; ESI-MS: 431 [M+H]$^+$ Intermediate 4.2

Linear Dimer 5'-OH-3'-TBS-imidazopyridazinon-β-D-ribofuranoside-(2'→5')-cyanoethyl-phosphorothioate-2'-TBS-3'-H-phosphonate-purine-β-D-ribofuranoside

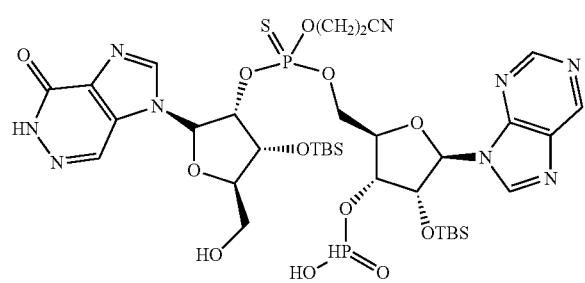

INTERMEDIATE 4.2 was prepared analogously to INTERMEDIATE 1.6 by using INTERMEDIATE 1.4 and the above described INTERMEDIATE 4.1 as starting materials.

LC-MS analytics of the raw material confirmed the presence of INTERMEDIATE 4.2 as a mixture of diastereoisomers.
LC-MS (system B):
INTERMEDIATE 4.2-a: $t_{Ret}$=14.86 min; INTERMEDIATE 4.2-b: $t_{Ret}$=15.01 min;
ESI-MS: 944 [M+H]$^+$ for each diastereoisomer Intermediate 4.3

Cyclic Dimer 3'-TBS-imidazopyridazinon-β-D-ribofuranoside-(2'→5')-cyanoethyl-phosphoro-thioate-2'-TBS-purine-β-D-ribofuranoside-(3'→5')-phosphorothioate

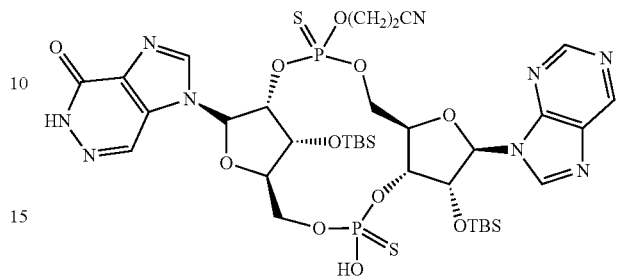

INTERMEDIATE 4.3 (as mixture of diastereomers) was prepared analogously to INTERMEDIATE 1.7 by using INTERMEDIATE 4.2 as starting material.
LC-MS (system B):
INTERMEDIATE 4.3-a: $t_{Ret}$=15.76 min; INTERMEDIATE 4.3-b: $t_{Ret}$=16.61 min;
INTERMEDIATE 4.3-c: $t_{Ret}$=17.68 min; INTERMEDIATE 4.3-d: $t_{Ret}$=19.26 min;
ESI-MS: 958 [M+H]$^+$ for each diastereoisomer.

Intermediate 4.4

Cyclic Dimer 3'-TBS-imidazopyridazinon-β-D-ribofuranoside-(2'→5')-phosphorothioate-2'-TBS-purine-β-D-ribofuranoside-(3'→5')-phosphorothioate

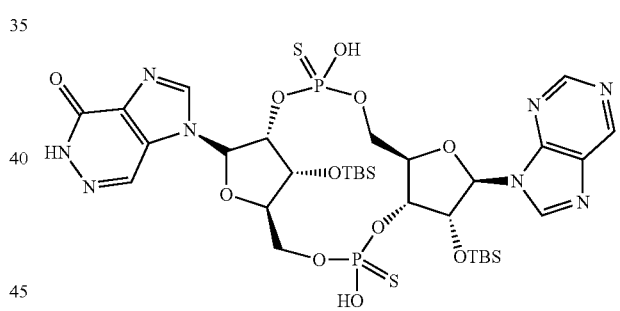

INTERMEDIATE 4.4 (as mixture of diastereomers) was prepared analogously to INTERMEDIATE 1.8 by using INTERMEDIATE 4.3 as starting material.
LC-MS (system B):
INTERMEDIATE 4.4-a: $t_{Ret}$=10.31 min; INTERMEDIATE 4.4-b: $t_{Ret}$=11.82 min;
INTERMEDIATE 4.4-c: $t_{Ret}$=12.26 min; INTERMEDIATE 4.4-d: $t_{Ret}$=14.47 min;
ESI-MS: 905 [M+H]$^+$ for each diastereoisomer.

SYNTHESES OF COMPOUNDS ACCORDING TO THE PRESENT INVENTION

General remark: The following pairs of compounds are diastereomers and differ with respect to the configuration of at least one phosphor atom, respectively:
EXAMPLE 1.1 and EXAMPLE 1.2;
EXAMPLE 2.1 and EXAMPLE 2.2;
EXAMPLE 3.1 and EXAMPLE 3.2;
EXAMPLE 4.1 and EXAMPLE 4.2.

Example 1.1 and Example 1.2

Cyclic (imidazopyridazinon-β-D-ribofuranoside-(2'→5')-phosphorothioate-adenosine-(3'→5')-phosphorothioate)

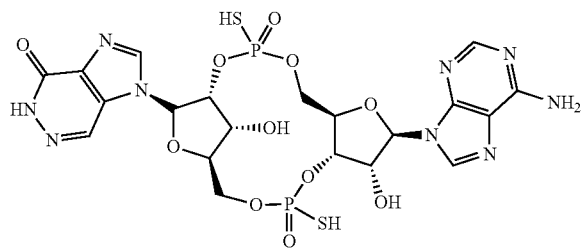

30 mL anhydrous pyridine and 15 mL anhydrous triethylamine were added to crude 3'-TBS-imidazopyridazinon-β-D-ribofuranoside-(2'→5')-phosphorothioate-2'-TBS-adenosine-(3'→5')-phosphorothioate (INTERMEDIATE 1.8; 0.76 g). The resulting solution was concentrated under reduced pressure to approximately 5 mL total volume, followed by simultaneous addition of triethylamine trihydrofluoride (3.590 mL, 21.7 mmol) and 11 mL anhydrous triethylamine. This solution was stirred at 50° C. for 3.5 hours. After cooling to room temperature, the reaction was quenched with methoxytrimethylsilane (10 mL, 72.4 mmol) and further stirred at room temperature to consume any excess of HF. After 30 minutes, all volatile components were evaporated under reduced pressure, followed by a final co-evaporation with 50 mL anhydrous toluene under reduced pressure. The residue was further dried in vacuo to yield the raw mixture containing Example 1.1 and Example 1.2.

65 mL water was added and the resulting suspension was placed in an ultrasonic bath at room temperature. After 15 minutes, this suspension was poured into 60 mL chloroform and the organic phase was separated. This extraction was repeated another two times with chloroform. The combined organic phases were extracted with 50 mL water and the combined product-containing aqueous phase was filtered with a 0.45 µm Rotilabo®-CME-syringe filter (outer diameter: 33 mm) to remove particulate components. The product solution was diluted with water to 500 mL and applied to a Q Sepharose™ Fast Flow anion exchange column (40-165 µm; 125×35 mm; 120 mL) Cl⁻-form, previously regenerated with 2 M sodium chloride and washed with water. The column was washed with water (2 column volumes), followed by a gradient of 0-1 M triethylammonium bicarbonate buffer (TEAB, pH 7) in water over column volumes (detection wavelength 254 nm). EXAMPLE 1.1 and EXAMPLE 1.2 eluted as mixture of isomers with ~0.6 M TEAB. Product-containing fractions were carefully concentrated to a final volume of approximately 10 mL under reduced pressure.

Separation of EXAMPLE 1.1 (fourth eluting) and EXAMPLE 1.2 (third eluting) was accomplished by repeated semi-preparative reversed phase HPLC purifications. The product solution was applied to a YMC*GEL ODS-A 12 nm column (10 µm; 250×16 mm; ~50 mL), previously equilibrated with 4% acetonitrile, 20 mM triethylammonium formate (TEAF, pH 6.8) in water. Elution was performed with a step-gradient of 4%, 6% and 20% acetonitrile, 20 mM TEAF (pH 6.8) in water Preparation of Example 1.1, Sodium Salt ("Fourth Eluting Diastereomer")

Desalting of EXAMPLE 1.1, TEA-salt was performed by preparative reversed phase medium pressure liquid chromatography (MPLC). The product solution (~40 mL) was applied to a Merck LiChroprep®RP-18 column (15-25 µm; 450×25 mm; ~220 mL), previously equilibrated with water. The column was washed with water to remove excess TEAF buffer. Afterwards, 2% 2-propanol in water was used to elute the desalted EXAMPLE 1.1. Product-containing fractions were partially concentrated under reduced pressure and subsequently applied to a SP Sepharose™ Fast Flow cation exchange column (45-165 µm; 125×35 mm; ~120 mL) Na⁺-form, previously regenerated with 2 M sodium chloride and washed with water. The column was washed with water until no UV-absorbance was detectable anymore (detection wavelength 254 nm). Product-containing fractions were carefully evaporated under reduced pressure and additionally dried in vacuo to yield EXAMPLE 1.1 as disodium salt.

HPLC (configuration A): $t_{Ret}$=8.56 min;
ESI-MS: 692 [M+H]⁺
¹H NMR (400 MHz, 318 K, 500 µL (CD₃)₂SO+30 µL D₂O) δ 8.70 (s, 1H), 8.63 (s, 1H), 8.34 (s, 1H), 8.16 (s, 1H), 6.07 (d, J=8.4 Hz, 1H), 5.91 (d, J=7.5 Hz, 1H), 5.07-4.99 (m, 2H), 4.95 (dd, J=7.5, 4.5 Hz, 1H), 4.44 (d, J=4.4 Hz, 1H), 4.33-4.21 (m, 3H), 4.05-3.93 (m, 1H), 3.92-3.77 (m, 2H) ppm.
³¹P NMR (162 MHz, D₂O): δ 52.4 (s, 1P), 55.3 (s, 1P) ppm.

Preparation of Example 1.2, Sodium Salt ("Third Eluting Diastereomer")

Desalting and salt change from TEA to sodium of EXAMPLE 1.2, TEA salt was performed in similar fashion as described for EXAMPLE 1.1, TEA salt.

HPLC (configuration A): $t_{Ret}$=7.75 min;
ESI-MS: 692 [M+H]⁺
¹H NMR (400 MHz, 318 K, 500 µL (CD₃)₂SO+30 µL D₂O) δ 8.72 (s, 1H), 8.59 (s, 1H), 8.33 (s, 1H), 8.15 (s, 1H), 6.04 (d, J=8.4 Hz, 1H), 5.88 (d, J=8.2 Hz, 1H), 5.25 (dd, J=8.5, 4.4 Hz, 1H), 5.08 (ddd, J=11.2, 8.4, 4.5 Hz, 1H), 4.92 (dd, J=8.2, 4.3 Hz, 1H), 4.37-4.27 (m, 1H), 4.27-4.21 (m, 3H), 4.08 (dd, J=11.0, 4.2 Hz, 1H), 3.82-3.77 (m, 1H), 3.67-3.60 (m, 1H) ppm.
³¹P NMR (162 MHz, D₂O): δ 55.8 (s, 1P), 57.0 (s, 1P) ppm.

Example 2.1 and Example 2.2

Cyclic (imidazopyridazinon-β-D-ribofuranoside-(2'→5')-phosphorothioate-2'-F-2'-deoxyadenosine-(3'→5')-phosphorothioate

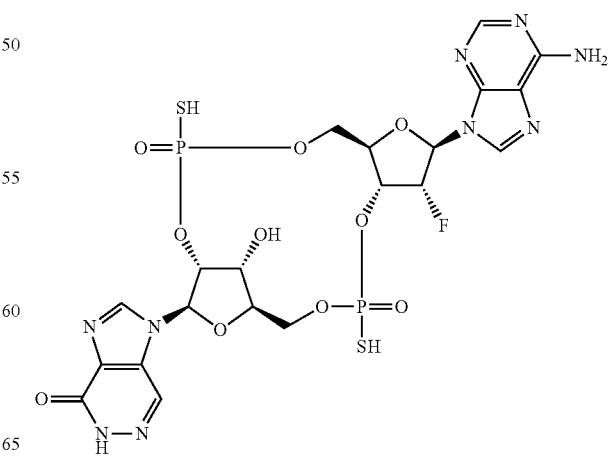

16 mg (19 μmol) of INTERMEDIATE 2.4-d were added to 1 mL anhydrous pyridine and 4 mL anhydrous acetonitrile and the solvent was azeotropically evaporated in vacuo. The residue was twice re-suspended in 10 mL anhydrous acetonitrile and again azeotropically evaporated in vacuo. 80.7 μL (1.0 mmol) anhydrous pyridine and 168 μL (1.2 μmol) TEA were added to the residue before 103 μL (0.63 mmol) TEA*3HF were cautiously added via a syringe. The resulting mixture was stirred at 50° C. for 90 min. After cooling to room temperature, the reaction was quenched by the addition of 20 mL of an aq. solution of triethylammonium carbonate (conc.=1 mol/L). The resulting mixture was stirred for further 15 min at room temperature. The mixture was carefully loaded on a Water Sep Pak C18© cartridge (5 g C18-material, preconditioned with first 25 mL acetonitrile and afterwards with 25 mL water) and washed with 60 mL of water. Afterwards the product was eluted from the cartridge by using 100 mL of a acetonitrile/triethylammonium acetat/water mixture (prepared by adding 1 mL of an aq. triethylammonium acetat solution (conc=1 mol/L) to 100 mL water and 25 mL acetonitrile). Fractions containing product were combined and the solvent was removed by lyophilization. The resulting product was further purified by prep. HPLC (Atlantis C18; 20 mM aq. NH4OAc/acetonitrile=98/2→80/20.). After the solvent were removed by freeze drying the product was dissolved in 2 mL water and poured on a Bio-Rad Spin column (filled with 250 mg BT AG 50W-2 resin 100-200 Mesh hydrogen Form, conditioned with 3 mL 1M aq. NaOH and afterwards washed with 6 mL water resulting in pH~7)) and eluted with 12 mL water. Fractions containing the final product were combined and the solvent was removed by freeze drying.

Example 2.1:

LC-MS (system C):

tRet=0.61 min; ESI-MS: 694 [M+H]+

1H NMR (400 MHz, 303 K, D$_2$O) δ ppm 8.73 (s, 1 H), 8.53 (s, 1 H), 8.24 (s, 1 H), 7.96 (s, 1 H), 6.40 (d, J=15.9 Hz, 1 H), 6.26 (d, J=8.6 Hz, 1 H), 5.55 (dd, J=51.1, 3.8 Hz, 1 H), 4.83-4.99 (m, 2 H), 4.75 (d, J=4.2 Hz, 1 H), 4.65 (ddd, J=12.2, 9.0, 2.2 Hz, 1 H), 4.53-4.59 (m, 2 H), 4.43-4.48 (m, 1 H), 4.16-4.24 (m, 2 H)

$^{31}$P NMR (162 MHz, D$_2$O): δ 55.7 (s, 1P), 52.2 (s, 1P) ppm.

Example 2.2

EXAMPLE 2.2 was prepared analogously to EXAMPLE 2.1 by using INTERMEDIATE 2.4-c as starting material.

LC-MS (system C):

t$_{Ret}$=0.30 min; ESI-MS: 694 [M+H]+

1H NMR (400 MHz, 303K, D$_2$O) δ ppm 8.80 (s, 1 H), 8.55 (s, 1 H), 8.24 (s, 1 H), 8.24 (s, 1 H), 6.44 (d, J=15.0 Hz, 1 H), 6.28 (d, J=8.5 Hz, 1 H), 5.54-5.73 (m, 1 H), 4.99-5.10 (m, 2 H), 4.64-4.70 (m, 1 H), 4.58 (d, J=4.4 Hz, 1 H), 4.52-4.57 (m, 2 H), 4.37-4.45 (m, 1 H), 4.22 (ddd, J=12.3, 3.5, 1.1 Hz, 1 H), 4.08 (ddd, J=11.7, 3.6, 1.7 Hz, 1H)

$^{31}$P NMR (162 MHz, D$_2$O): δ 55.5 (s, 1P), 55.9 (s, 1P) ppm.

Example 3.1 and Example 3.2

Cyclic (imidazopyridazinon-β-D-ribofuranoside-(2'→5')-phosphorothioate-LNA-adenine-(3'→5')-phosphorothioate), Sodium Salt

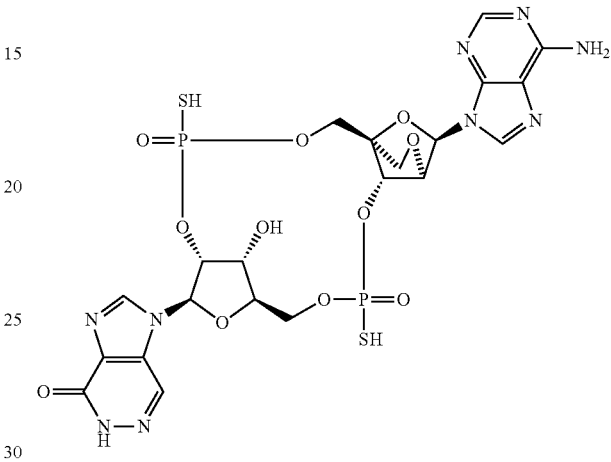

EXAMPLES 3.1 and 3.2 were prepared analogously to EXAMPLE 2.1 and 2.2 by using INTERMEDIATE 3.4-d (for EXAMPLE 3-1) and 3.4-c (for EXAMPLE 3-2) as starting material, respectively.

Example 3.1:

LC-MS (system E):

t$_{Ret}$=0.37 min; ESI-MS: 704 [M+H]+

1H NMR (400 MHz, 303 K, D$_2$O) δ ppm 8.79 (s, 1 H), 8.53 (s, 1 H), 8.22 (s, 1 H), 7.95 (s, 1 H), 6.26 (d, J=8.4 Hz, 1 H), 6.14 (s, 1 H), 5.08 (s, 1 H), 4.97 (ddd, J=9.6, 8.4, 4.4 Hz, 1 H), 4.81 (d, J=5.4 Hz, 1 H), 4.82-4.70 (m, 3 H), 4.55 (d, J=2.0 Hz, 1 H), 4.35 (dd, J=11.9, 2.7 Hz, 1 H), 4.25-4.16 (m, 3 H), 4.08 (d, J=8.5 Hz, 1 H) $^{31}$P NMR (162 MHz, D$_2$O): δ 56.0 (s, 1P), 53.0 (s, 1P) ppm.

Example 3.2:

LC-MS (system E):

t$_{Ret}$=0.29 min; ESI-MS: 704 [M+H]+

1H NMR (400 MHz, 303 K, D$_2$O) δ ppm 8.85 (s, 1 H), 8.56 (s, 1 H), 8.23 (s, 1 H), 8.15 (s, 1 H), 6.26 (d, J=8.4 Hz, 1 H), 6.16 (s, 1 H), 5.20 (s, 1 H), 5.00 (ddd, J=13.0, 8.4, 4.5 Hz, 1 H), 4.87 (d, J=5.0 Hz, 1 H), 4.83-4.73 (m, 2 H), 4.62 (d, J=4.5 Hz, 1 H), 4.54-4.52 (m, 1 H), 4.47 (dd, J=11.3, 5.0 Hz, 1 H), 4.27-4.20 (m, 2 H), 4.12 (dd, J=11.3, 3.1 Hz, 1 H), 4.10 (d, J=8.5 Hz, 1 H).

$^{31}$P NMR (162 MHz, D$_2$O): δ 57.3 (s, 1P), 55.8 (s, 1P) ppm.

Example 4.1 and Example 4.2

Cyclic (imidazopyridazinon-β-D-ribofuranoside-(2'→5')-phosphorothioate-purine-β-D ribofuranoside-(3'→5')-phosphorothioate), Sodium Salt

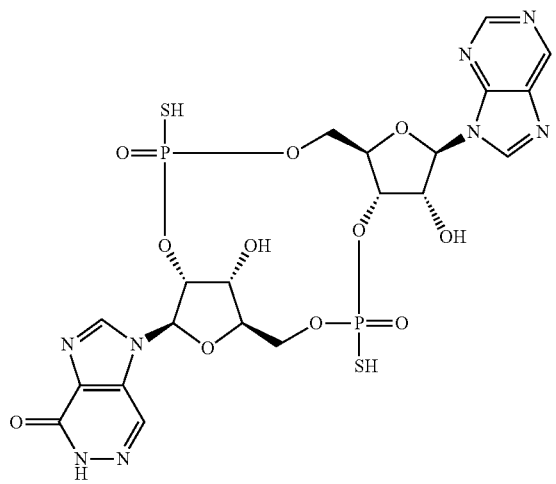 [SMILES: O=c1[nH]ncc2c1ncn2[C@@H]1O[C@@H]2COP(=O)(S)O[C@H]3[C@@H](O)[C@H](n4cnc5cncnc54)O[C@@H]3COP(=O)(S)O[C@@H]1[C@@H]2O]

EXAMPLES 4.1 and 4.2 were prepared analogously to EXAMPLE 1.1 and 1.2 by using INTERMEDIATE 4.4-d and INTERMEDIATE 4.4-c as starting material. In addition to the procedure described for EXAMPLES 1.1 and 1.2, before starting the reaction the starting material was once azeotroped by using a 2:1 mixture of anhydrous pyridine and anhydrous triethylamine.

Example 4.1:

HPLC (configuration B): $t_{Ret}$=10.22 min;

ESI-MS: 677 [M+H]+

$^1$H NMR (400 MHz, 318 K, 500 μL (CD$_3$)$_2$SO+30 μL D$_2$O) δ 9.16 (s, 1H), 8.95 (s, 1H), 8.82 (s, 1H), 8.68 (s, 1H), 8.62 (s, 1H), 6.06 (d, J=8.3 Hz, 1H), 6.06 (d, J=7.4 Hz, 1H), 5.11-4.98 (m, 3H), 4.44 (d, J=4.4 Hz, 1H), 4.34-4.25 (m, 3H), 4.08-3.97 (m, 1H), 3.93-3.83 (m, 1H), 3.84-3.77 (m, 1H).

$^{31}$P NMR (162 MHz, D$_2$O): δ 55.3 (s, 1P), 52.6 (s, 1P) ppm.

Example 4.2:

HPLC (configuration B): $t_{Ret}$=5.50 min;

ESI-MS: 677 [M+H]$^+$ $^1$H NMR (400 MHz, 318 K, 500 μL (CD$_3$)$_2$SO+30 μL D$_2$O) δ 9.16 (s, 1H), 8.94 (s, 1H), 8.82 (s, 1H), 8.72 (s, 1H), 8.59 (s, 1H), 6.04 (d, J=8.5 Hz, 1H), 6.03 (d, J=8.1 Hz, 1H), 5.30 (dd, J=8.5, 4.3 Hz, 1H), 5.09 (ddd, J=11.3, 8.4, 4.6 Hz, 1H), 5.01 (dd, J=8.2, 4.3 Hz, 1H), 4.45-4.32 (m, 1H), 4.32-4.19 (m, 3H), 4.13 (dd, J=11.0, 4.1 Hz, 1H), 3.84-3.75 (m, 1H), 3.71-3.61 (m, 1H).

$^{31}$P NMR (162 MHz, D$_2$O): δ 55.8 (s, 1P), 57.8 (s, 1P) ppm.

The invention claimed is:

1. A compound of formula I

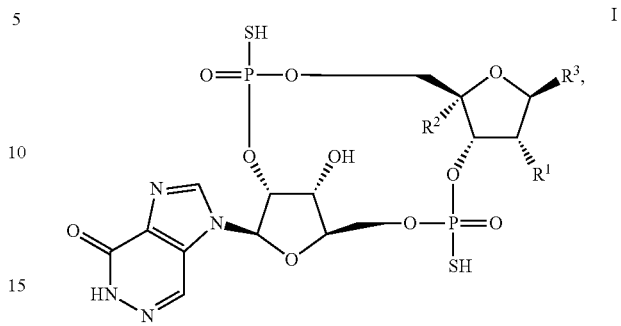

wherein
R$^1$ is selected from the group consisting of H, F, —O—C$_{1-3}$alkyl and OH, and
R$^2$ is H, or
R$^2$ is —CH$_2$— and R$^1$ is —O—, forming together a —CH$_2$—O— bridge, and
R$^3$ is a purine nucleobase selected from the group consisting of purine, adenine, guanine, xanthine and hypoxanthine, connected through its N$^9$ nitrogen,
or a salt thereof.

2. The compound of claim 1, wherein the compound is a substantially pure (Sp,Sp), (Rp,Rp), (Sp,Rp), or (Rp,Sp) stereoisomer, or a salt thereof.

3. The compound of claim 1, wherein the compound is a substantially pure (Rp,Rp) stereoisomer, or a salt thereof.

4. The compound of claim 1, wherein the the salt is a pharmaceutically acceptable salt.

5. A pharmaceutical composition comprising one or more compounds according to claim 1, or one or more pharmaceutically acceptable salts thereof, optionally together with one or more inert carriers and/or diluents.

6. A method for treating diseases or conditions selected from the group consisting of inflammation, allergic diseases, autoimmune diseases, infectious diseases and cancer, in a patient in need thereof, comprising administering to the patient a compound according to claim 1.

7. A vaccine comprising a compound according claim 1.

8. A pharmaceutical composition comprising one or more compounds according to claim 1 and one or more additional therapeutic agents, optionally together with one or more inert carriers and/or diluents.

9. A pharmaceutical composition comprising one compound according to claim 1 and one or more additional therapeutic agents.

10. A compound according to claim 1 of formula Ia:

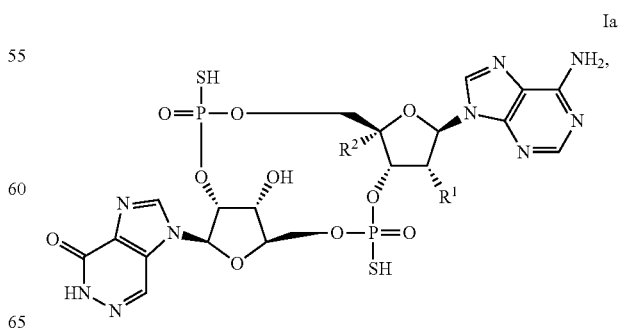

or a salt thereof.

11. The compound of claim 10, wherein the compound is a substantially pure (Sp,Sp), (Rp,Rp), (Sp,Rp), or (Rp,Sp) stereoisomer, or a salt thereof.

12. The compound of claim 10, wherein the compound is a substantially pure (Rp,Rp) stereoisomer, or a salt thereof.

13. The compound of claim 10, wherein the salt is a pharmaceutically acceptable salt.

14. A pharmaceutical composition comprising one or more compounds according to claim 10, or one or more pharmaceutically acceptable salts thereof, optionally together with one or more inert carriers and/or diluents.

15. A method for treating diseases or conditions selected from the group consisting of inflammation, allergic diseases, autoimmune diseases, infectious diseases and cancer, in a patient in need thereof, comprising administering to the patient a compound according to claim 10.

16. A vaccine comprising a compound according to claim 10.

17. A pharmaceutical composition comprising one or more compounds according to claim 10 and one or more additional therapeutic agents, optionally together with one or more inert carriers and/or diluents.

18. A pharmaceutical composition according to claim 17 comprising one compound according to claim 10 and one or more additional therapeutic agents.

19. A compound according to claim 1 of formula Ib

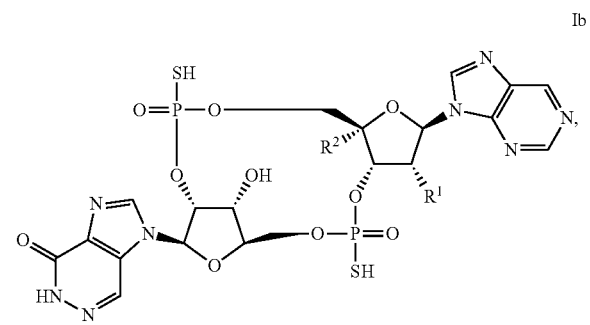

or a salt thereof.

20. The compound of claim 19, wherein the compound is a substantially pure (Sp,Sp), (Rp,Rp), (Sp,Rp), or (Rp,Sp) stereoisomer, or a salt thereof.

21. The compound of claim 19, wherein the compound is a substantially pure (Rp,Rp) stereoisomer, or a salt thereof.

22. The compound of claim 19, wherein the salt is a pharmaceutically acceptable salt.

23. A pharmaceutical composition comprising one or more compounds according to claim 19, or one or more pharmaceutically acceptable salts thereof, optionally together with one or more inert carriers and/or diluents.

24. A method for treating diseases or conditions selected from the group consisting of inflammation, allergic diseases, autoimmune diseases, infectious diseases and cancer, in a patient in need thereof, comprising administering to the patient a compound according to claim 19.

25. A vaccine comprising a compound according to claim 19.

26. A pharmaceutical composition comprising one or more compounds according to claim 19 and one or more additional therapeutic agents, optionally together with one or more inert carriers and/or diluents.

27. A pharmaceutical composition according to claim 26 comprising one compound according to claim 19 and one or more additional therapeutic agents.

28. A compound of formula Ia.1:

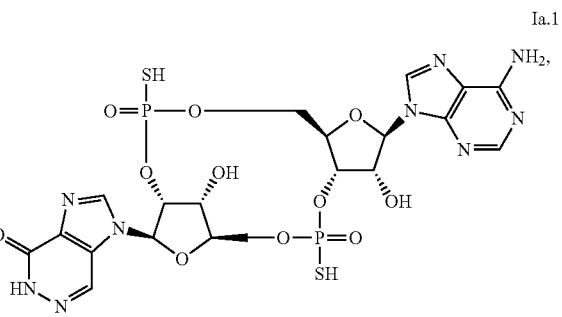

wherein the compound is a substantially pure (Rp,Rp), (Rp,Sp), (Sp,Rp) or (Sp,Sp) stereoisomer, or any mixtures thereof, or a salt thereof.

29. The compound of claim 28 wherein the compound is a substantially pure (Rp,Rp) stereoisomer, or a salt thereof.

30. The compound of claim 28, wherein the salt is a pharmaceutically acceptable salt.

31. The compound of claim 28, wherein the salt is a sodium salt.

32. The compound of claim 29, wherein the salt is a sodium salt.

33. A compound of formula Ia.2

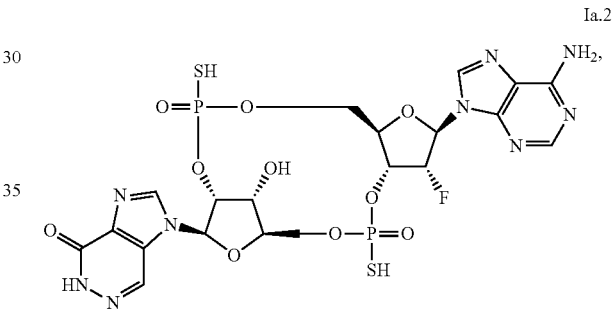

wherein the compound is a substantially pure (Rp,Rp), (Rp,Sp), (Sp,Rp) or (Sp,Sp) stereoisomer, or any mixtures thereof, or a salt thereof.

34. The compound of claim 33, wherein the compound is a substantially pure (Rp,Rp) stereoisomer, or a salt thereof.

35. The compound of claim 33, wherein the salt is a pharmaceutically acceptable salt.

36. The compound of claim 33, wherein the salt is a sodium salt.

37. The compound of claim 34, wherein the salt is a sodium salt.

38. A compound of formula Ia.3

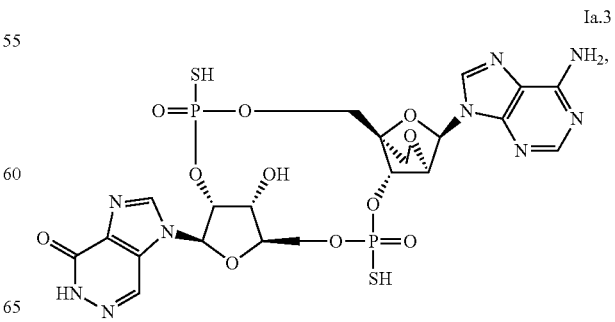

wherein the compound is a substantially pure (Rp,Rp), (Rp,Sp), (Sp,Rp) or (Sp,Sp) stereoisomer, or any mixtures thereof, or a salt thereof.

39. The compound of claim 38, wherein the compound is a substantially pure (Rp,Rp) stereoisomer or a salt thereof.

40. The compound of claim 38, wherein the salt is a pharmaceutically acceptable salt.

41. The compound of claim 38, wherein the salt is a sodium salt.

42. The compound of claim 39, wherein the salt is a sodium salt.

43. A compound of formula Ib.1

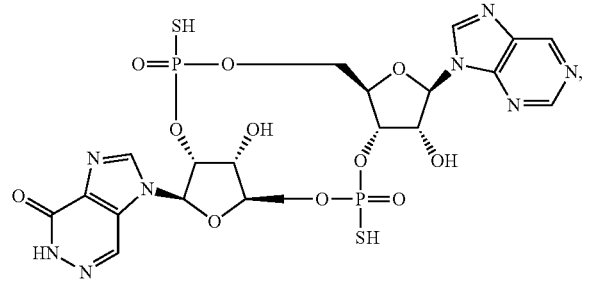

wherein the compound is a substantially pure (Rp,Rp), (Rp,Sp), (Sp,Rp) or (Sp,Sp) stereoisomer, or any mixtures thereof, a salt thereof.

44. The compound of claim 43, wherein the compound is a substantially pure (Rp,Rp) stereoisomer or a salt thereof.

45. The compound of claim 43, wherein the salt is a pharmaceutically acceptable salt.

46. The compound of claim 43, wherein the salt is a sodium salt.

47. The compound of claim 44, wherein the salt is a sodium salt.

48. A compound of formula Ia.1:

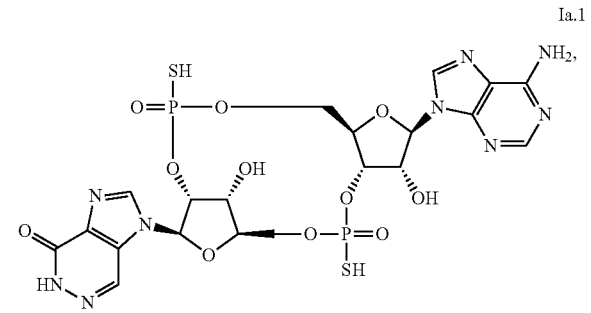 [SMILES: Nc1ncnc2c1ncn2[C@@H]1O[C@@H]2COP(=O)(S)O[C@@H]3[C@H](O)[C@@H](COP(=O)(S)O[C@H]2[C@H]1O)O[C@H]3n1cnc2c(=O)[nH]ncc21]

wherein the compound is a substantially pure (Rp,Rp), (Rp,Sp), (Sp,Rp) or (Sp,Sp) stereoisomer, or any mixtures thereof.

49. The compound of claim 48, wherein the compound is a substantially pure (Rp,Rp) stereoisomer.

50. A compound of formula Ia.2

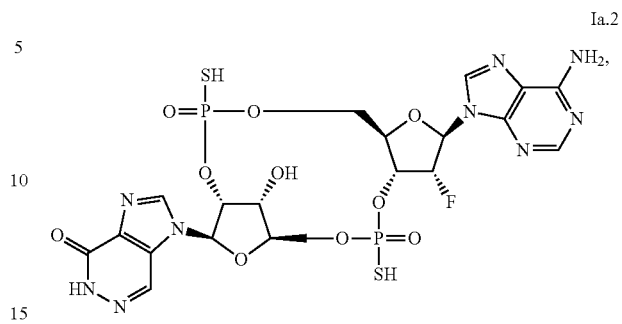

wherein the compound is a substantially pure (Rp,Rp), (Rp,Sp), (Sp,Rp) or (Sp,Sp) stereoisomer, or any mixtures thereof.

51. The compound of claim 50, wherein the compound is a substantially pure (Rp,Rp) stereoisomer.

52. A compound of formula Ia.3

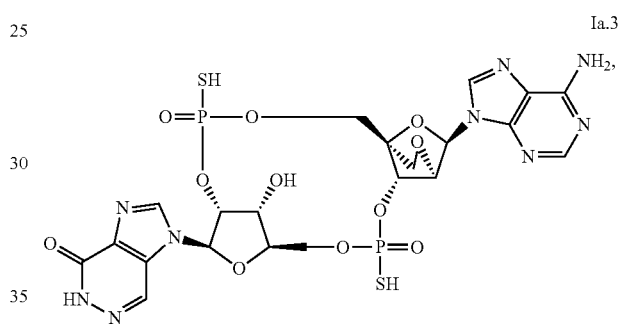

wherein the compound is a substantially pure (Rp,Rp), (Rp,Sp), (Sp,Rp) or (Sp,Sp) stereoisomer, or any mixtures thereof.

53. The compound of claim 52, wherein the compound is a substantially pure (Rp,Rp) stereoisomer.

54. A compound of formula Ib.1

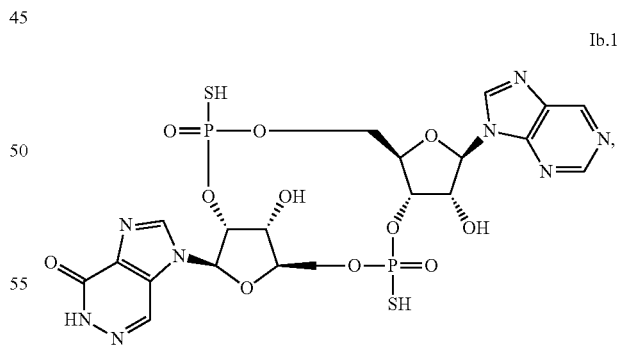

wherein the compound is a substantially pure (Rp,Rp), (Rp,Sp), (Sp,Rp) or (Sp,Sp) stereoisomer, or any mixtures thereof.

55. The compound of claim 54, wherein the compound is a substantially pure (Rp,Rp) stereoisomer.

* * * * *